United States Patent [19]

Khanna et al.

[11] Patent Number: 5,258,518

[45] Date of Patent: Nov. 2, 1993

[54] 2-SUBSTITUTED TERTIARY CARBINOL DERIVATIVES OF DEOXYNOJIRIMYCIN

[75] Inventors: Ish K. Khanna, Vernon Hills; Richard A. Mueller, Glencoe; Richard M. Weier, Lake Bluff, all of Ill.

[73] Assignee: G. D. Searle & Co., Skokie, Ill.

[21] Appl. No.: 861,058

[22] Filed: Apr. 1, 1992

[51] Int. Cl.$^5$ .............. C07D 213/69; C07D 211/46; C07D 491/056; A61K 31/70; A61K 31/445
[52] U.S. Cl. ................... 546/242; 546/116; 546/220; 546/219; 514/885; 514/315; 514/318; 514/328; 514/302
[58] Field of Search ............. 546/116, 219, 220, 242; 514/885

[56] References Cited

U.S. PATENT DOCUMENTS

| | | | |
|---|---|---|---|
| 4,182,763 | 1/1980 | Casten et al. | 424/251 |
| 4,260,622 | 4/1981 | Junge et al. | 546/220 X |
| 4,328,233 | 5/1982 | Boshagen et al. | 546/220 X |
| 4,407,809 | 10/1983 | Junge et al. | 546/220 X |
| 4,533,668 | 8/1985 | Matsumara et al. | 546/220 X |
| 4,639,436 | 1/1987 | Junge et al. | 546/116 X |
| 4,806,650 | 2/1989 | Schroder et al. | 546/219 X |
| 4,849,430 | 7/1989 | Fleet et al. | 514/315 |
| 4,861,892 | 8/1989 | Fleet | 546/219 X |
| 4,871,747 | 10/1989 | Kinast et al. | 546/220 X |
| 4,957,926 | 9/1990 | Jacob et al. | 514/315 |
| 5,003,072 | 3/1991 | Partis et al. | 546/243 |
| 5,011,829 | 4/1991 | Hirsch et al. | 514/50 |
| 5,025,021 | 6/1991 | Getman et al. | 546/116 X |
| 5,026,713 | 6/1991 | Getman et al. | 514/302 |
| 5,030,638 | 7/1991 | Partis et al. | 514/315 |

OTHER PUBLICATIONS

Fleet et al., II, Febs Letters, vol. 237, pp. 128–132 (1988).

*Primary Examiner*—Floyd D. Higel
*Attorney, Agent, or Firm*—Scott J. Meyer

[57] ABSTRACT

2-Substituted tertiary carbinol derivatives of deoxynojirimycin are disclosed having the formula

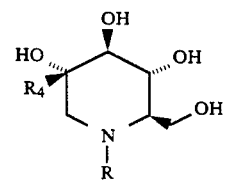

wherein
$R_4$ = an alkyl, vinyl, alkenyl, alkynyl, aryl, aralkyl, alkenylalkyl, alkylnylalkyl or $CH_2Y$ substituent having from about 1 to 10 carbon atoms;
Y = OR', SR', NR'R', or $N_3$;
R' = H or $CH_3$; and
R = H or an alkyl, aralkyl, alkenylalkyl, alkynylalkyl, aralkenyl, aralkynyl or hydroxyalkyl substituent, having from about 1 to 18 carbon atoms, provided that no carbon unsaturated bond is directly attached to nitrogen.

These compounds have useful antiviral activity as demonstrated against lentivirus.

10 Claims, No Drawings

2-SUBSTITUTED TERTIARY CARBINOL DERIVATIVES OF DEOXYNOJIRIMYCIN

BACKGROUND OF THE INVENTION

This invention relates to novel 2-substituted tertiary carbinol derivatives of 1,5-dideoxy-1,5-imino-D-glucitol and, more particularly, to the chemical synthesis of these derivatives and intermediates therefor, and to their method of inhibiting viruses such as lentiviruses.

1,5-dideoxy-1,5-imino-D-glucitol-(deoxynojirimycin or DNJ) and its N-alkyl and O-acylated derivatives are known inhibitors of viruses such as human immunodeficiency virus (HIV). See, e.g., U.S. Pat. Nos. 4,849,430; 5,003,072; 5,030,638 and PCT Int'l. Appln. WO 87/03903. Several of these derivatives also are effective against other viruses such as HSV and CMV as disclosed in U.S. Pat. No. 4,957,926. In some cases antiviral activity is enhanced by combination of the DNJ derivative with other antiviral agents such as AZT as described in U.S. Pat. No. 5,011,829. Various of these DNJ derivative compounds also have antihyperglycemic activity. See, e.g., U.S. Pat. Nos. 4,182,763, 4,533,668 and 4,639,436.

Notwithstanding the foregoing. the search continues for the discovery and novel synthesis of new and improved antiviral compounds.

BRIEF DESCRIPTION OF THE INVENTION

In accordance with the present invention, novel 2-substituted tertiary carbinol derivatives of 1,5-dideoxy-1,5-imino-D-glucitol are provided. According to another embodiment of the invention, novel methods of chemical synthesis of these DNJ derivatives and their intermediates are provided. The novel DNJ derivatives and various of their intermediates have useful antiviral activity as demonstrated against lentivirus.

The 2-substituted tertiary carbinol derivatives of 1,5-dideoxy-1,5-imino-D-glucitol can be represented by the following general structural Formula I:

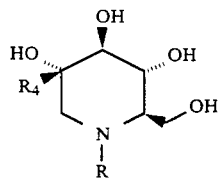

wherein $R_4$ = an alkyl, vinyl, alkenyl, alkynyl, aryl, aralkyl, alkenylalkyl, alkynylalkyl or $CH_2Y$ substituent having from about 1 to 10 carbon atoms;

Y = OR', SR', NR'R', or $N_3$;

R' = H or $CH_3$; and

R = H or an alkyl, aralkyl, alkenylalkyl, alkynylalkyl, aralkenyl, aralkynyl or hydroxyalkyl substituent having about 1 to 18 carbon atoms, provided that no carbon unsaturated bond is directly attached to nitrogen.

In Formula I, the alkyl moieties in the R substituents preferably are straight chain or branched alkyl groups or cycloalkyl groups which preferably have from one to about 8 carbon atoms, e.g., methyl, ethyl, propyl, isopropyl, n-butyl, iso-butyl, sec.-butyl, tert-butyl, pentyl, hexyl, heptyl, octyl, 2-ethylbutyl, 2-methylpentyl, cyclopentyl and cyclohexyl, and which can contain one or more heteroatoms, e.g. O, S, N. The alkyl moieties in the $R_4$ substituents preferably have from one to about 4 carbon atoms, e.g., methyl, ethyl, isopropyl and sec.-butyl. The corresponding alkenyl moieties in Formula I are, e.g., ethenyl, propenyl, butenyl, pentenyl, hexenyl, and the corresponding alkynyl moieties are, e.g., ethynyl, propynyl, butynyl, pentynyl, hexynyl, and their alkyl-substituted derivatives, e.g. methylbutenyl and methylbutynyl.

Also in Formula I, the aryl moieties in the R and $R_4$ substituents preferably are phenyl and substituted phenyl, e.g., lower alkylphenyl such as 2-methylphenyl and 2,4-dimethylphenyl; halophenyl such as 2-chlorophenyl, 4-chlorophenyl, 2,4-dichlorophenyl, 2-bromophenyl, 4-fluorophenyl, 2,4-difluoromethylphenyl and trifluoromethylphenyl; methoxyphenyl and nitrophenyl.

Preferred compounds of Formula I are the following:

1,5-Dideoxy-1,5-imino-2-C-methyl-D-glucitol,
1,5-Butylimino-1,5-dideoxy-2-C-methyl-D-glucitol,
1,5-Dideoxy-i,5-(3-phenylpropylimino)-2-C-methyl-D-glucitol, and
1,5-Dideoxy-1,5-(2-ethylbutylimino)-2-C-methyl-D-glucitol.

The novel synthesis of compounds of Formula I comprises the stereoselective addition of an organometallic reagent, e.g. a Grignard reagent, to the carbonyl at C-2. The substituent at C-3 strongly influences the stereochemical configuration at C-2. The unambiguous assignment of absolute stereochemistry at C-2 in these novel compounds and intermediates used in their preparation has been established by a series of NMR tests including spin decoupling. For description of these conventional techniques (e.g., NOESY and COSY), see e g., Neuhaus and Williamson, "The Nuclear Overhauser Effect in Structural and Conformational Analysis," VCH Publishers, New York, 1989; and Martin and Zektzer, "Two-Dimensional NMR Methods for Establishing Molecular Connectivity," VCH Publishers, New York, 1988.

In accordance with a preferred embodiment of the invention, the compounds of Formula I can be chemically synthesized by the sequence of reactions shown in the following Reaction Scheme A (or 2-part Reaction Scheme B), in which the numbers in parentheses refer to the compounds defined by the generic formula shown above said numbers. $R_1$, $R_2$, $R_3$, $R_5$, X and W in Reaction Scheme A-B can be any alkyl or aryl group such as illustrated by the reactants and products described hereinafter.

In accordance with another aspect of the invention, novel pro-drugs of the antiviral compounds of Formula I are prepared by 0-acylation of their free hydroxyl groups.

Scheme A:
Generic Synthesis of 2-substituted tert-carbinol 1,5-iminosugars.
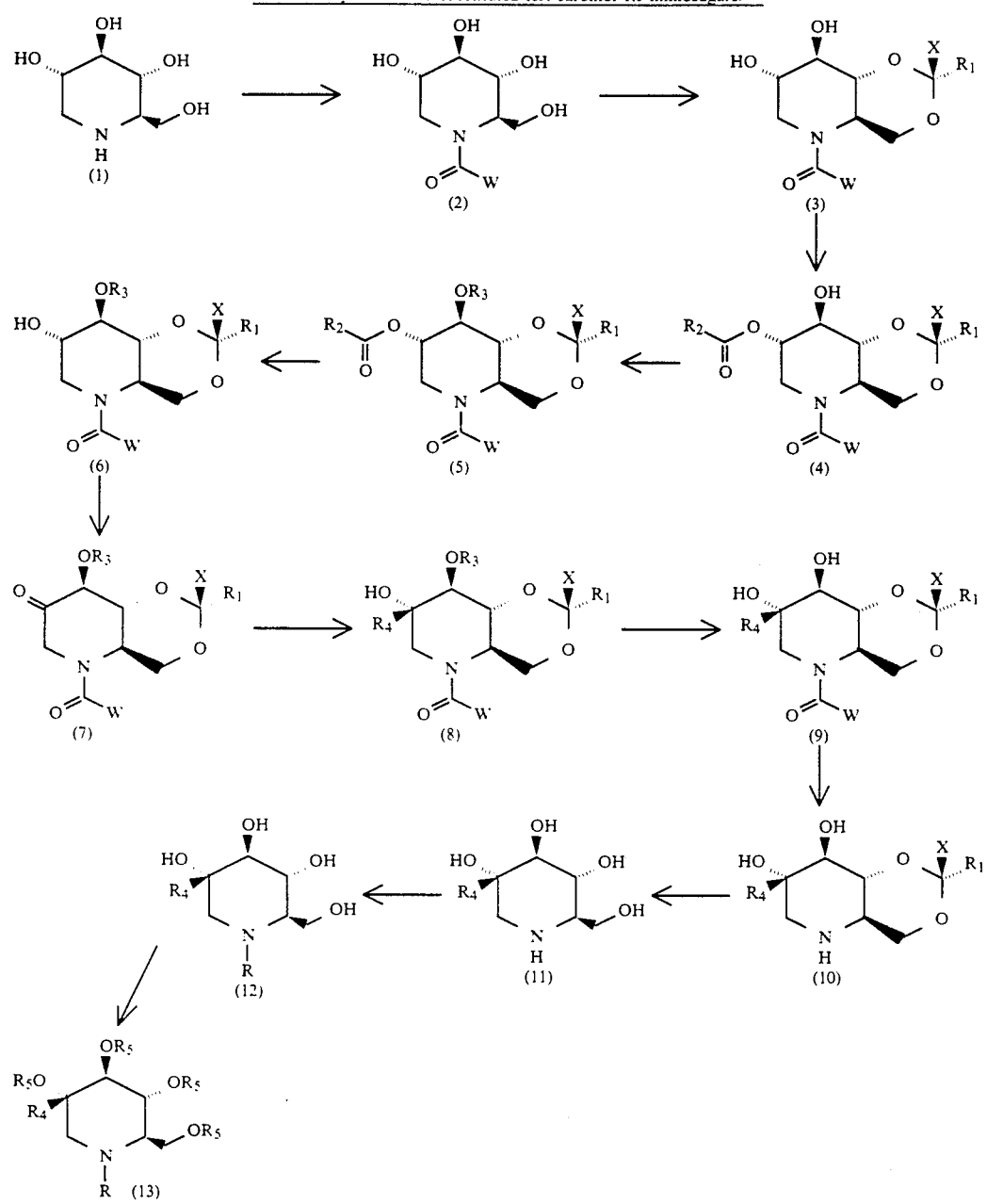
Scheme B:
General Synthesis of 2-substituted tert-carbinol 1,5-iminosugars.
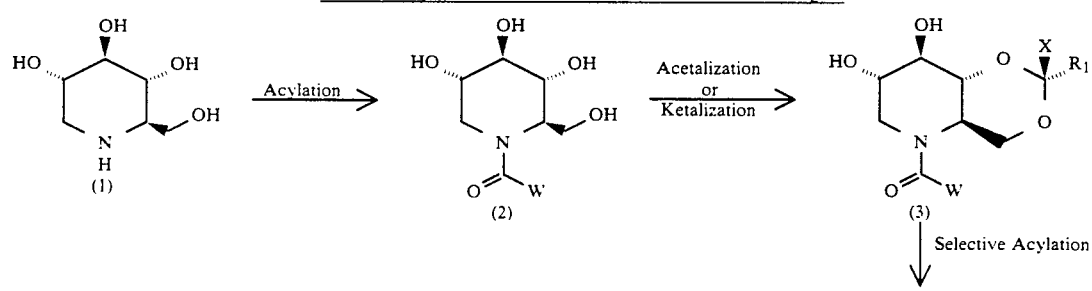

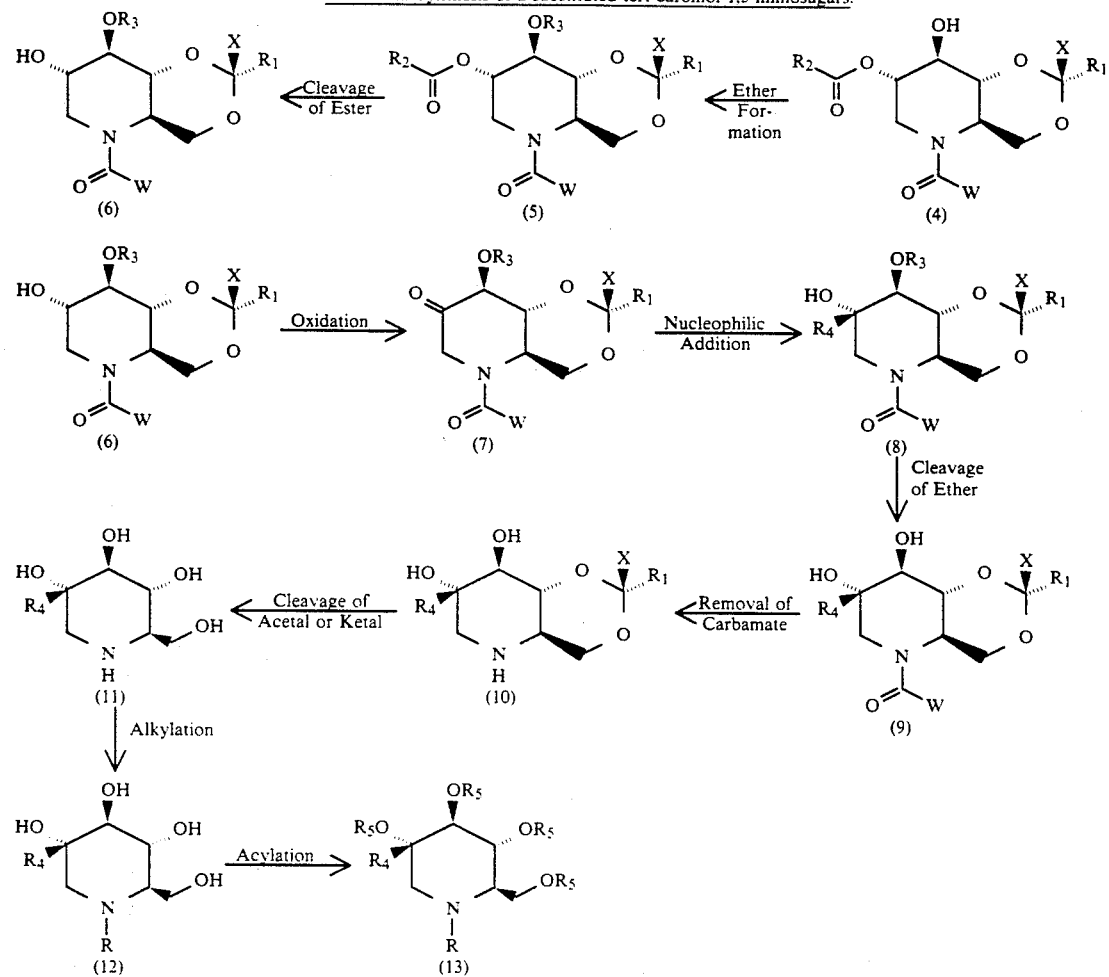

-continued
Scheme B:
General Synthesis of 2-substituted tert-carbinol 1,5-iminosugars.

The foregoing Reaction Scheme A-B comprises the following general reaction steps (a) The starting material, DNJ (1), is N-acylated with an acylating agent to form an amide or carbamate derivative of DNJ (2);
(b) The hydroxyls at C-4 and C-6 are protected with a hydroxyl protecting agent by acetalization or ketalization to form an acetal or ketal (3);
(c) The hydroxyl at C-2 is selectively protected by O-acylation with an acylating agent at C-2 to give novel intermediate (4);
(d) The hydroxyl at C-3 is protected by ether formation to produce the fully protected novel derivative (5);
(e) The protecting group at C-2 is selectively removed by cleavage of ester or carbonate to give novel product (6);
(f) The free hydroxyl group at C-2 is oxidized to give novel ketone (7);
(g) The stereoselective addition of the desired $R_4$ is carried out by nucleophilic addition at C-2 to form the novel 2-substituted tertiary carbinol (8);
(h) The hydroxyl protecting group at C-3 is selectively removed by cleavage of ether to form novel product (9);
(i) The N-carbamate group is cleaved to give novel intermediate (10);
(j) The hydroxyl protecting group at C-4 and C-6 is removed by cleavage of acetal or ketal to give the novel intermediate (11);
(k) Intermediate (11) is N-alkylated to give the desired novel antiviral 2-substituted tertiary carbinol derivatives of DNJ, viz. compounds (12).
(l) The free hydroxyl groups in the 2-substituted tertiary carbinol derivatives of DNJ (12) can be partially or fully O-acylated to give novel compounds (13).

The sequence of steps (h), (i), (j) and (k), involving cleavage of various protecting groups to give intermediates (9), (10), (11) and (12), can be interchanged or combined.

Illustrative reaction conditions for carrying out the synthesis steps of Reaction Scheme A-B are as follows:

N-Acylation of DNJ (1) in step (a) can be carried out by conventional N-acylation procedures well known to those skilled in the art. Suitable general procedures for acylation of amines are described in U.S. Pat. No. 5,003,072; March, J. in *Advanced Organic Chemistry*, Wiley, New York, 1985; Patai, S. (Ed.) in *The Chemistry of Amides*, Wiley, New York, 1970. For example, DNJ is N-acylated to form an amide, carbamate or thiocarbamate using a variety of reagents such as acyl halides (e.g., acetyl chloride, propionyl bromide, benzoyl chloride or butyryl chloride), anhydrides (e.g., acetic anhydride, propionic anhydride or butyric anhydride), chloroformates (e.g., methyl chloroformate, ethyl chloroformate, vinyl chloroformate, benzyl chloroformate) or dicarbonates (e.g., di-tert-butyl dicarbonate). The reaction of DNJ with acyl halides is preferentially carried out in the presence of non-polar, aprotic solvents such as ethers (e.g., diethyl ether, tetrahydrofuran, dioxane, dimethoxyethane, dibutylether, tert-butyl methyl ether), chlorinated solvents (e.g., methylene chloride, chloroform, carbon tetrachloride) or hydrocarbon solvents (e.g., benzene, toluene). However, the reaction of DNJ (1) with anhydrides, chloroformates or dicarbonates is preferentially carried out by dissolving in one or more of polar, protic solvents (such as water, methanol, ethanol) and in the presence of a base (e.g, potassium carbonate, lithium carbonate, sodium carbonate, cesium carbonate, triethylamine, pyridine, 4-dimethylaminopyridine, diisopropylethylamine, i,8-diazabicyclo[5,4,0]undec-7-ene). N-Acylation is preferentially carried out by reacting DNJ (1) with alkyl or aryl chloroformate in solvents such as DMF or aqueous sodium bicarbonate at 20°-50° C. to give the product (2).

Protection of the hydroxyl groups at C-4 and C-6 in step (b) to give acetal or ketal derivative (3) can be carried out by conventional hydroxyl protection procedures such as those described, e. g., in U.S. Pat. No. 5,003,072 and in Green, T. W., *Protective Groups in Organic Synthesis*, Wiley, New York, 1981. or 2d ed., 1991. The cyclic acetals and ketals are formed by the reaction of 4,6-dihydroxy compound (2) with an aldehyde or a ketone in the presence of an acid catalyst. Illustrative carbonyl (or carbonyl equivalents such as dimethyl acetal or dimethyl ketal) compounds useful in this reaction are benzaldehyde, 4-methoxybenzaldehyde, 2,4-dimethoxybenzaldehyde, 4-dimethylaminobenzaldehyde, 2-nitrobenzaldehyde, 2,2,2-trichloroacetaldehyde (chloral) and acetophenone. The acid catalysts suitable for this reaction are, e.g., para-toluene sulfonic acid, cat. HCl, cat. sulfuric acid, $FeCl_3$, $ZnCl_2$, $SnCl_2$ and $BF_3$-etherate, and the reaction is carried out in the presence of aprotic solvents such as methylene chloride, 1,2-dimethoxyethane, dioxane, dimethylformamide, acetonitrile, dimethylacetamide or dimethylsulfoxide. Thus para-toluene sulfonic acid is added to a solution of benzaldehyde dimethyl acetal in organic medium, e.g., dimethylformamide, and reacted with N-acyl-DNJ (2) at 20°-65° C. to give the product (3).

The selective protection of hydroxy group at C-2 in compound (3) in step (c) can be carried out by reaction with O-acylation forming esters (such as acetate, chloroacetate, dichloroacetate, trichloroacetate, methoxyacetate, phenoxyacetate, 4-chlorophenoxyacetate, isobutyrate, pivolate, benzoate, 4-phenylbenzoate, 4-methylbensoate, 4-chlorobenzoate, 4-nitrobenzoate, and the like) and carbonates (such as methyl, ethyl, 2,2,2-trichloroethyl, isobutyl, vinyl, allyl, phenyl, benzyl, 4-methoxybenzyl and the like) using acid chloride, anhydrides or chloroformates The selective acylation at C-2 can be carried out by using conventional acylation procedures such as described e.g., in U.S. Pat. No. 5,025,021. Two preferred methods are as follows:

Method A- Compound (3) is refluxed with dibutyltin oxide in solvents (such as benzene, toluene, xylene, methanol or ethanol and the like) to form a homogenous solution. The stannylene intermediate is then reacted at 0°-50° C. in the presence of a base (such as triethylamine, pyridine, 4-dimethylaminopyridine, 1,8-diazabicyclo[5,4,0]undec-7-ene or diisopropylethylamine) and an acylating agent (such as acetyl chloride, benzoyl chloride, pivaloyl chloride, chloroacetyl chloride, acetic anhydride, isobutyric anhydride, methyl chloroformate, ethyl chloroformate isobutylchlorofomate, phenyl chloroformate, benzyl chloroformate and the like) to provide selective protection at C-2 and give the novel intermediate (4).

Method B - A solution of co (3) and tetrabutylammonium iodide in a chlorinated solvent such as methylene chloride, 1,2-dichloroethane or carbon tetrachloride is reacted with an acylating agent, e.g., benzoyl chloride, under basic conditions, e.g., with potassium carbonate, sodium carbonate-or cesium carbonate to provide 2-O-acyl protection selectively at C-2 and give the novel intermediate (4).

Protection of the hydroxyl group at C-3 in step (d) can be carried out by forming an ether (e.g., methoxymethyl, metylthiomethyl, benzyl, benzyloxymethyl, 2,2,2-trichloroethoxymethyl, 2-methoxyethoxymethyl (MEM), 2-(trimethylsilyl)ethoxymethyl (SEM), triethylsilyl, tert-butyldimethylsilyl (TBDMS), tert-butyldiphenylsilyl, triisopropylsilyl, isopropyldimethylsilyl, methyldiisopropylsilyl or methyldi-tert-butylsilyl using conventional hydroxyl protection procedures (see, e.g., Green, T. W., *Protective Groups in Organic Synthesis*, Wiley, New York, 1981, 2d ed., 1991). Thus the intermediate compound (4) can be reacted with a protecting agent, e.g., 2-methoxyethoxymethyl chloride, 2-(trimethylsilyl)ethoxymethyl chloride, tert-butyldimethylsilyl trifluoromethnesulfonate or triisopropylsilyl trifluoromethnesulfonate to give the novel fully protected intermediate (5). This ether formation is preferably carried out in the presence of a non-polar, aprotic solvent (e. g., diethyl ether, tetrahydrofuran, dioxane, dimethoxyethane, dibutylether, tert-butyl methyl ether, methylene chloride, chloroform or carbon tetrachloride) using a base (such as triethylamine, pyridine, 4-dimethylaminopyridine, 1,8-diazabicyclo[5,4,0]undec-7-ene or diisopropylethylamine) at temperature of 0°-50° C.

Selective removal of the protecting group (ester or carbonate) at C-2 in step (e) can be carried out by reaction of the intermediate (5) tetrabutylammonium hydroxide in aqueous dioxane or with other bases, e.g., aqueous sodium hydroxide, aqueous potassium hydroxide, aqueous potassium carbonate, aqueous lithium hydroxide, aqueous lithium carbonate, ammonium hydroxide or aqueous methylamine (with or without the presence of organic solvents such as methanol, ethanol or dioxane) to give the novel intermediate (6). The acetate group at C-2 can also be removed by reaction with potassium cyanide or sodium cyanide or by enzymatic reaction with lipases. Various of the carbonates at C-2 can also be removed by special conditions. For example, 2,2,2-trichloroethyl carbonate can be cleaved by treatment with zinc in methanol.

Since the rest of the molecule is fully protected, the oxidation of the secondary alcohol in (6) can be successfully carried out in step (f) by reaction with a variety of oxidizing agents [see, e.g., March, J. in *Advanced Organic Chemistry*, Wiley, New York, 1985; House, H. O. in *Modern Synthetic Reactions*, Benzamin Publishing Co., Mass., 1972; Augustine, R. L. in *Oxidations—Techniques and Applications in Organic Synthesis*, Dekker, New York, 1969;W. P. Griffith and S. M. Levy, *Aldrichchimica Acta* 23. 13 (1990); R. M. Moriarty and O. Prakash, *J. Org. Chem.* 50, 151, (1985); A. Mancuso, D.

Swern, *Synthesis* 165, (1981); S. Czernecki, C. Georgoulus, C. L. Stevens and K. Vijayakantam, *Tetrahedron Lett.* 26, 1699 (1985); J. Herscovici, M. J. Egra and K. Antonakis, *J. Chem. Soc. Perkin Trans* 1, 1967 (1982); E. J. Corey, E. Barrette and P. Magriotis, *Tetrahedron Lett.* 26, 5855 (1985); and H. Tomioka, K. Oshima and H. Nozaki, *Tetrahedron Lett.* 25, 539 (1982)]. Illustrative of the reagents suitable for oxidation of the C-2 hydroxyl in compound (6) are pyridinium chlorochromate (with or without additives such as sodium acetate, celite, alumina or molecular sieves), pyridinium dichromate, chromium trioxide/pyridine, 2,2'-bipyridinium chlorochromate, cyclic chromate ester [E. J. C E Barrette and P. Magriotis, *Tetrahedron Lett.* 26, 5855 (1985)], $RuCl_2(PPh_3)_3$-tert-BuOOH, silver carbonate on celite, cerium (IV) ammonium nitrate (with or without sodium bromate), tetra-n-propylammonium perruthenate and activated dimethyl sulfoxide reagents (using DMSO and one of the electrophilic reagents such as acetic anhydride, trifluoroacetic anhydride [TFAA], oxalyl chloride, trifluorosulfonic anhydride or dicyclohexylcarbodiimide). Formation of the novel carbonyl compound (7) is preferentially carried out by oxidation of the hydroxyl group at C-2 in (6) with trifluoroacetic anhydride in dimethylsulfoxide (DMSO) using methylene chloride as solvent at $-70°$ to $0°$ C.

The introduction of alkyl ($C_1$-$C_4$), vinyl, alkynyl, aryl, aralkyl, and other $R_4$ groups at C-2 in compound (8) in step (g) can be achieved by stereoselective addition of organometallic reagents ($R_4M$) to the 2-keto derivative (7) using conventional procedures (see, e. g., E. C. Ashby and J. T. *Chemical Reviews*, 75, 521(1975); K. Maruoka, Y. Araki, and H. Yamamoto, *Tetrahedron Lett.* 29, 3101 (1988) K. Maruoka, T. Itoh, and H. Yamamoto, *J. Am. Chem. Soc* 107, 4576 (1985)]. For example, 2-substituted tertiary carbinol derivatives (8) can be prepared by reaction of carbonyl compound (7) with Grignard reagents (e.g., methylmagnesium chloride, methylmagnesium bromide, ethylmagnesium bromide, isobutylmagnesium bromide. phenylmagnesium bromide, vinylmagnesium bromide or allylmagnesium bromide) in aprotic, non-polar solvent (e. g., diethyl ether, tetrahydrofuran, dioxane, dimethoxyethane, dibutylether, methyl ether or benzene) at $-70°$ to $20°$ C. Other organometallic reagents such as methyl lithium, acetylide, sodium acetylide, ethylenediamine complex, dimethyl magnesium, trimethyl aluminum, organozinc and organocadmium reagents obtained by addition of Grignard reagents ($R_4MgCl$) with zinc and cadmium halides, ate complexes such as $MeLi-Me_2CuLi$, $LiMg(CH_3)_2$, $LiAl(i-C_4H_9)_3CH_3$ and $LiAl(CH_3)_4$, can also be used to give the addition product (8).

The protecting group at C-3 in compound (8) is then removed in step (h) by appropriate selection of reagents to give the novel compound (9). For example, trialkylsilyl ethers and SEM ether in (8) can be removed by reagents carrying a fluoride source, such as tetrabutylammmonium fluoride, CsF, terabutylammonium chloride/KF, $LiBF_4$ or $Ph_3C^+BF_4^-$ or Pyridine+HF to give (9). Methylthiomethyl ether can preferably be cleaved with mercuric chloride or silver nitrate Similarly, 2,2,2-trichloromethoxymethyl ether can be cleaved by heating with Zn-Cu or Zn-Ag in methanol. Benzyl, substituted benzyl or benzyloxymethyl ethers can preferably be removed by catalytic hydrogenation procedures (using $H_2$, Pd/C in solvents such as ethanol, methanol, isopropanol and tetrahydrofuran). This catalytic hydrogenation procedure to remove the benzyl ether is further useful because it simultaneously removes the N-protecting carbobenzoxy group from the compound (8) ($W=OCH_2Ph$) and yields the novel intermediate(10) directly. If the hydroxyl group at C-3 is protected as methoxymethyl or 2-methoxyethoxyethyl ether, it can preferably be removed by aqueous acid (80% AcOH) or Lewis acid catalyzed cleavage (using $ZnBr_2$, $TiCl_4$ or $HBF_4$) after the carbamate hydrolysis (of N-1) or the reduction (of amide at N-1 to the corresponding tertiary amine) of compound (8).

The nitrogen protecting carbamate group in compound (9) can be easily removed in step (i) by base hydrolysis at temperature of $40°$ to $100°$ C. to give the novel compound (10). Illustrative bases suitable for this reaction are aqueous sodium hydroxide, lithium hydroxide or potassium hydroxide with or without the presence of organic solvents such as methanol, ethanol, ethylene glycol and dioxane. The carbamates can also be cleaved by other reagents such as sulfur nucleophile's (e.g., sodium thiomethoxide and lithium thiopropoxide) or iodotrimethylsilane. Benzyl or substituted benzyl carbamates can be removed by base hydrolysis as mentioned above or by catalytic hydrogenation procedures, e.g. $H_2$ and Pd/C or $H_2$ and Pd black.

The acetal or ketal group from the intermediate (10) can be removed in step (j) to give the novel intermediate (11) by using the following conditions elaborated for the individual group. For example, the cleavage of benzylidene group in (10) can preferably be carried out by using transfer hydrogenation in the presence of hydrogen donors such as cyclohexene or 1,4-cyclohexadiene. Thus, the benzylidene intermediate (10) is refluxed with $Pd(OH)_2$ in ethanol and cyclohexene to give the novel intermediate (11). The benzylidine group in (10) can similarly be removed by using metals (such as Li, Na or K) and liquid ammonia at $-70°$ to $-30°$ C. to give (11). The benzylidene acetal can also be cleaved using N-bromosuccinimide and $BaCO_3$ or $CaCO_3$) in carbon tetrachloride or by electrochemical reduction. 2,2,2-Trichloroethylidine acetal is preferably cleaved by catalytic reduction ($H_2$, Raney Ni) using aqueous sodium hydroxide and ethanol. Alternately, the intermediate (9) ($R_1=Ph$, $X=H$, $W=OCH_2Ph$) can be directly converted to (11) using either transfer hydrogenation [$Pd(OH)_2$, cyclohexene] or Na/ammonia reduction. Similarly, the preferred intermediate (25) (in generic formula 8, $R_3=CH_2Ph$, $R_1=Ph$, $X=H$, $W=OCH_2Ph$) can also be converted to (11) in one step sequence using transfer hydrogenation or metal/ammonia reduction.

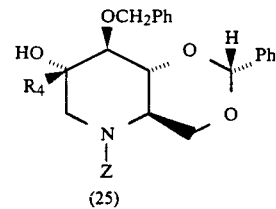

(25)

$Z = COOCH_2Ph$

N-Alkylation of intermediate (11) can be carried out in step (k) by reductive alkylation procedures using $NaCNBH_3$, $NaBH_4$, and alkylaldehyde or by catalytic hydrogenation procedures such as described, e.g., in U.S. Pat. Nos. 4,182,763; 4,639,436; 5,003,072; and 5,003,638. For example, the N-alkylation can be carried out by reacting intermediate (11) with an appropriate alkylaldehyde in the presence of a hydrogen donor reducing agent, e.g., catalytically activated hydrogen. Hydrogenation in the presence of a noble metal catalyst, e.g., palladium, at elevated pressure and temperature in methanol solvent medium is suitable. Appropriate alkylaldehydes for preparing the corresponding N-alkyl derivative compounds (12) are, e.g., n-propanal, n-butanal, n-pentanal, n-hexanal, n-heptanal and n-octanal. Thus, reaction of an aldehyde having an alkyl moiety corresponding to the desired R in Formula I with Pd on carbon in aqueous ethanol and THF is suitable procedure. Preferred aldehydes for this reaction are, e.g., butyraldehyde, 3-phenylpropionaldehyde and 2-ethylbutyraldehyde to prepare antiviral compounds (XVIA), (XVIB) and (XVIC), respectively.

Alternatively, N-alkylation can be achieved by reacting intermediate (11) with alkylhalide such as benzyl bromide, bromobutane, bromohexane, iodomethane and the like in the presence of a base such as triethylamine, pyridine and diisopropylethylamine. Suitable solvents for the reaction are, e.g., DMF, dimethylacetamide, dimethylsulfoxide and pyridine.

When the nitrogen in DNJ (1) is acylated as an amide [intermediate (2), W=alkyl aralkyl], the sequence to target 2-substituted tertiary carbinol derivatives proceeds as shown in Reaction Scheme A-B until the isolation of intermediate (9) ( W=alkyl, aralkyl). The sequence is then modified as illustrated in Reaction Scheme C.

novel intermediate (14) can also be prepared from the 2-alkyl carbinol derivative (11) by direct acylation using acyl halide (e.g., acetyl chloride, propionyl bromide, butyryl chloride or benzoyl chloride or anhydrides, e.g., acetic anhydride, propionic anhydride or butyric anhydride). The reaction of compound (11) with acyl halides is preferentially carried out in the presence of non-polar, aprotic solvents such as ethers, e.g., diethyl ether, tetrahydrofuran, dioxane, dimethoxyethane, dibutylether, tert-butyl methyl ether, or chlorinated solvents e.g., methylene chloride, chloroform and carbon tetrachlorid, or hydrocarbon solvents, e.g., benzene and toluene. However, the reaction of (11) with anhydrides is preferentially carried out by dissolving in one or more of polar, protic solvents such as water, methanol or ethanol and in the presence of base, e.g, potassium carbonate, lithium carbonate, sodium carbonate, cesium carbonate, triethylamine, pyridine, 4-dimethylaminopyridine, diisopropylethylamine or 1,8-diazabicyclo[5,4,0]undec-7-ene]. Alternately, the compound (9) is reduced first (preferably with borane-dimethyl sulfide complex) to give the intermediate (15) which is then subjected to deacetalization/ deketalization as illustrated above to give the compound (12A).

The compound (12) in Reaction Scheme A-B can be O-acylated (partially or fully) to give the novel compound (13) using conventional acylation procedures for acylation well known to those skilled in the art. Illustrative suitable general procedures for acylation of hydroxyl groups are described in U.S. Pat. 5,003,072;

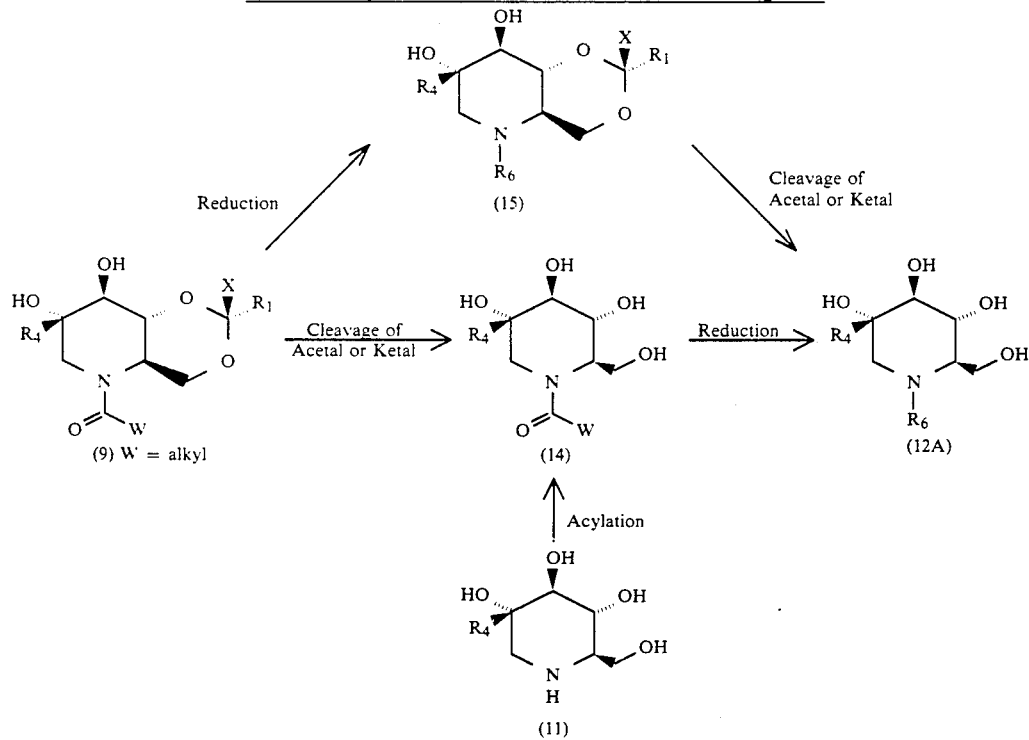

The acetal or ketal group from compound (9) is first removed following the conditions illustrated for the synthesis of compound (ii). The amide in the compound (14) so obtained is then reduced to alkyl derivative (12A, $R_6$=$CH_2R$) using reagents such as lithium aluminum hydride or borane-dimethyl sulfide complex. The March, J. in *Advanced Organic Chemistry*, Wiley, New York, 1985; Green, T. W., *Protective Groups in Organic Synthesis*, Wiley, New York, 1981, 2d ed., 1991. For example, the compound (12) can be O-acylated to form ester or carbonate using a variety of reagents such as acyl halides, e.g., acetyl chloride and propionyl bromide, pivaloyl chloride, benzoyl chloride and butyryl chloride, or anhydrides, e.g., acetic anhydride, propionic anhydride and butyric anhydride, or chloroformates, e.g., methyl chloroformate, ethyl chloroformate, vinyl chloroformate, phenyl chloroformate and benzyl chloroformate. The reaction of compound (12) with the acylating agent is preferentially carried out in the presence of a base (such as triethylamine, pyridine, 4-dimethylaminopyridine, diisopropylethylamine or 1,8-diazabicyclo[5,4,0]undec-7-ene]. The reaction can be carried out using the base as a solvent or having additional co-solvent, e.g., diethyl ether, tetrahydrofuran, dioxane, dimet dibutylether, tert-butyl methyl ether, methylene chloride, chloroform, carbon tetrachloride, benzene or toluene. This reaction is preferably be carried out at 20° to 90° C.

In the synthesis of preferred novel compounds of Formula I according to the steps of the general Reaction Scheme A-B, the preferred reaction conditions are set forth in the following Reaction Schemes D, E and F. Synthesis of the 2-keto DNJ analogs VIIA to VIID from the starting DNJ (I) in steps (a) through (f) is set forth in Reaction Scheme D. The stereoselective Grignard addition to the 2-keto DNJ analogs VIIA to VIID to produce the 2-substituted tertiary carbinol intermediates VIIIA to XIIB in step (g) is set forth in Reaction Scheme E. The synthesis of the 2-substituted tertiary carbinol derivatives of DNJ, compounds XVIA to XVIC, from the 2-substituted tertiary carbinol intermediate XIA in steps (h) to (k) is set forth in Reaction Scheme F. The compound XVIA is esterified to give the pro-drugs XVIIIA to XVIIIC. The intermediate XV is acylated to SVIIA and XVIIB which are reduced to novel antiviral compound 12A of Reaction Scheme C.

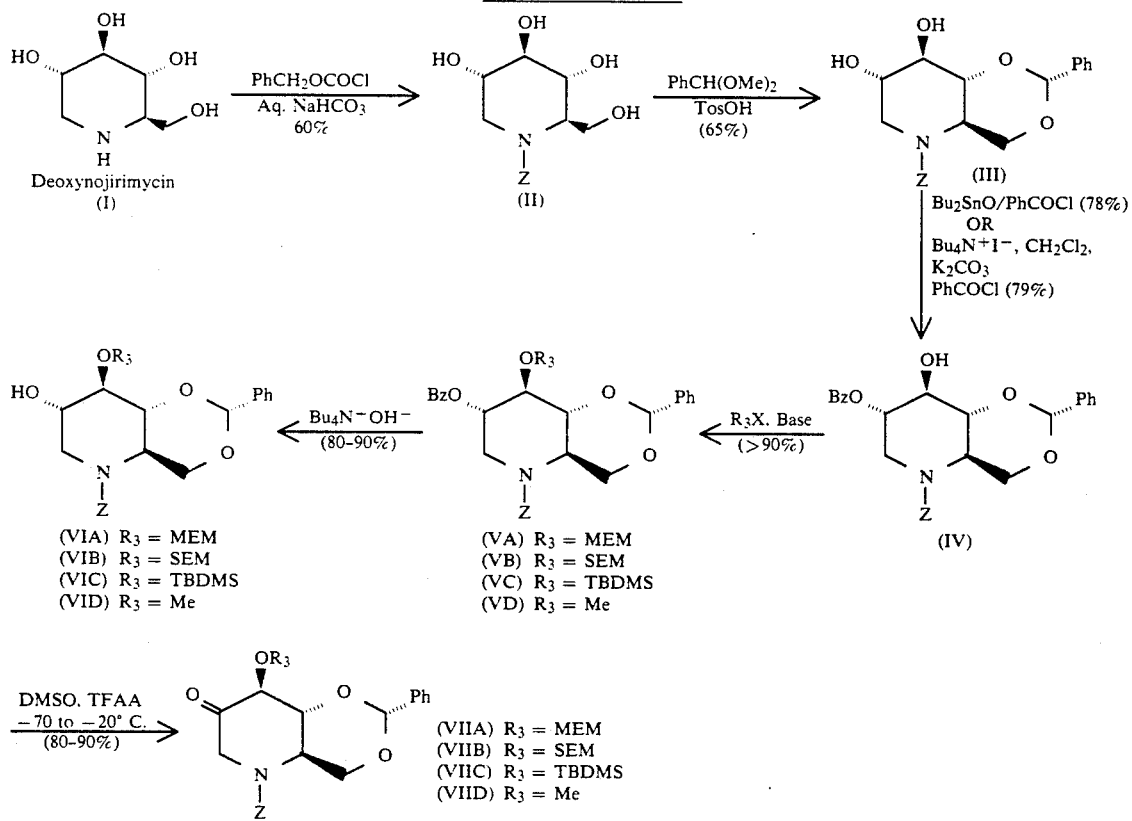

Scheme E: Nucleophilic Additions to 2-Ketone (VIIA–VIID) → (VIIIA–XIIA) + (VIIIB–XIIB)

| Compound (R₃) | Reagent | R₄ | Diastereomeric Ratio of products (A/B) | Chem. Yield (%) |
|---|---|---|---|---|
| –Si(Me)₂–C(Me)₃ (TBS) | MeMgX | Me | VIIIA/VIIIB = <15/85 | VIIIB = 62% |
| –Si(Me)₂–C(Me)₃ (TBS) | Me₃SiCH₂Li / CeCl₃ | CH₂SiMe₃ | IXA/IXB = <10/90 | IXB = 43% |
| –CH₂OCH₂CH₂OMe | MeMgX | Me | XA/XB = 33/67 | XA = 21% <br> XB = 43% |
| –CH₂OCH₂CH₂SiMe₃ | MeMgX | Me | XIA/XIB = 92/8 | XIA = 68% <br> XIB = 5.4% |
| Me | MeMgX | Me | XIIA/XIIB = 93/7 | XIIA = 54% <br> XIIB = 4% |

Scheme F: Synthesis of 2-Methyl Carbinols

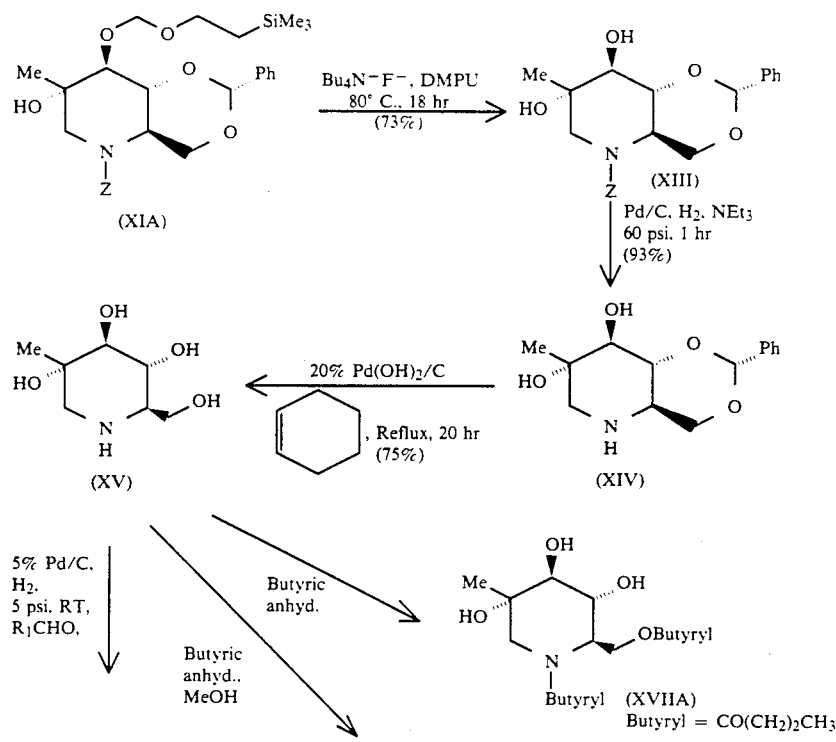

Scheme F: Synthesis of 2-Methyl Carbinols

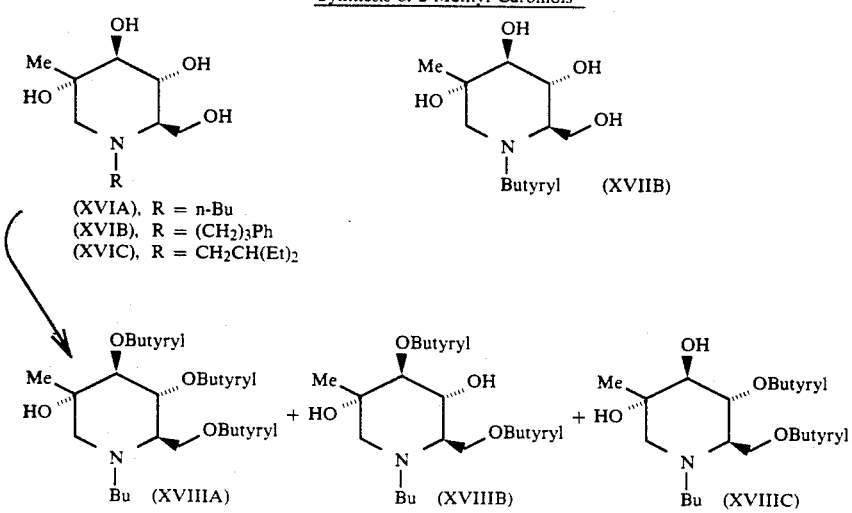

(XVIA), R = n-Bu
(XVIB), R = (CH₂)₃Ph
(XVIC), R = CH₂CH(Et)₂

Compounds of the following two structures can be synthesized by following the sequence of reaction steps and using the reaction conditions shown in Reaction Scheme F:

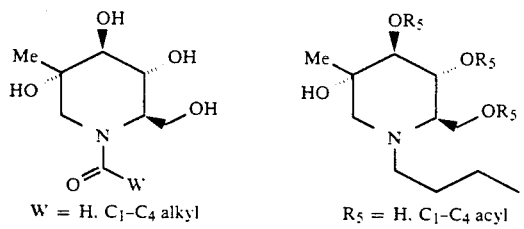

W = H, $C_1$–$C_4$ alkyl
$R_5$ = H, $C_1$–$C_4$ acyl

In the above formulas, alkyl preferably is propyl as in compounds (XVIIA) and (XVIIB) of Reaction Scheme F; and acyl preferably is butyryl as in compounds (XVIIIA), (XVIIIB) and (XVIIIC) of Reaction Scheme F In accordance with another embodiment of the invention, formation of the 2-substituted tertiary carbinols from the 2-keto derivative (7) can be carried out by alternate methods that involve elaboration of an olefin or opening of an epoxide. This method is illustrated by the following Reaction Scheme G:

Scheme G: Synthesis of 2-substituted tert-Carbinol from Olefin

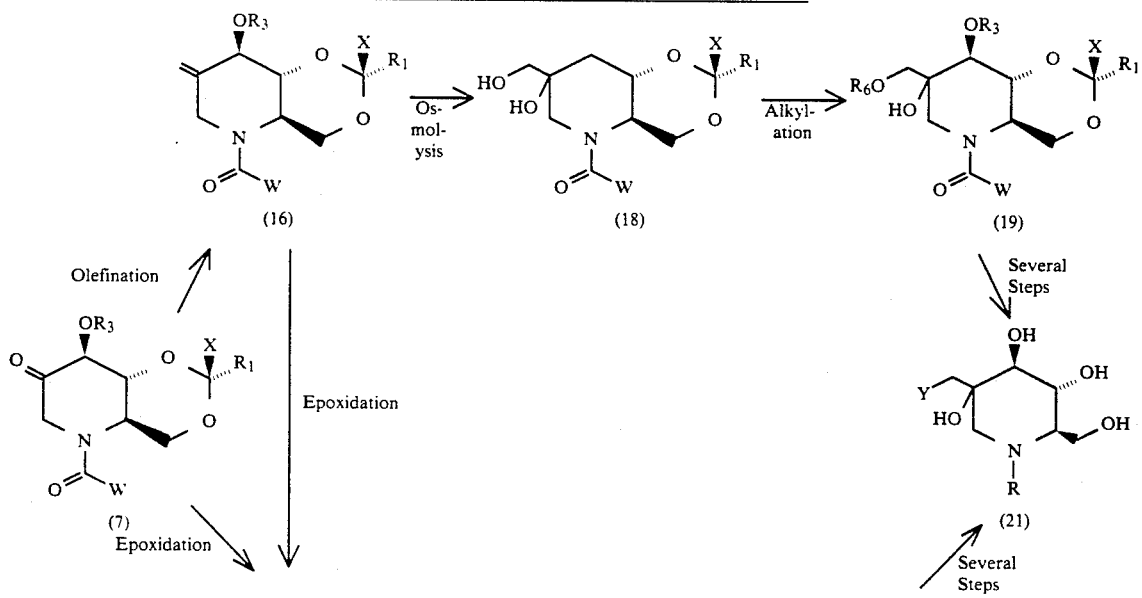

-continued
Scheme G:
Synthesis of 2-substituted tert-Carbinol from Olefin

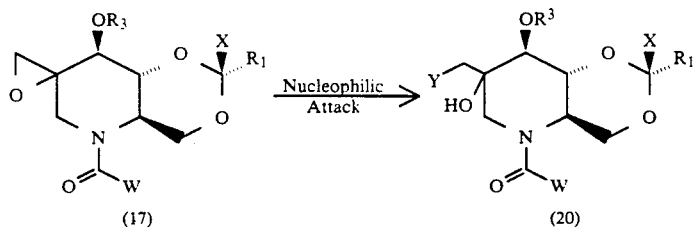

Reaction Scheme G comprises the following general reaction steps:

The ketone (7) is converted to novel olefinic compound (16). This conversion of compound (7) to the olefinic compound (16) can be achieved by a variety of methodologies such as by Wittig or modified Wittig olefination [see e.g., P. J. Murphy, J. Brennan, *Chem. Soc Rev.*, 17, 1, (1988)], using Tebbe's reagent [F. N. Tebbe, G. W. Parshall and G. S. Reddy, *J. Am. Chem. Soc.* 100, 3611, (1978)] or other titanium based reagents [e.g., L. Clawson, S. L. Buchwald and R. H. Grubbs, *Tetrahedron Lett.* 25, 5733, (1984) or zirconium promoted olefination [J. M. Tour, P. V. Bedworth and R. Wu, Tetrahedron Lett 30, 3927, (1989)].

Olefinic intermediate (16) is reacted with 3-chloroperbenzoic acid (MCPBA) in methylene chloride at room temperature to form the novel epoxide intermediate derivative (17). The epoxidation of the olefin can similarly be achieved by a number of other reagents such as dimethyldioxirane, peroxy acids [see, e.g., Rebeck et al. *J. Org. Chem.* 51, 1649 (1986)], Sharpless epoxidations using t-butylhydroperoxide [see, e.g., Katsuki and Sharpless, *J. Am. Chem. #Soc.* 102, 5974 (1980); Ibid. Vol. 109, 5675 (1987); Wang and Zhou, *Tetrahedron* 43, 2935 (1987); Finn and Sharpless, *J. Am. Chem. Soc.* 113, 113 (1991)]; and sulfamyloxaziridines (Davis et al., *Tetrahedron Lett.* 27, 5079 (1986)].

The ketone (7) can also be converted to the epoxide directly by using dimethyloxosulfonium methylide or dimethylsulfonium methylide [see, e.g., E. J. Corey and M. Chaykovsky, *J. Am. Chem. Soc.* 87, 1353 (1965)].

Both the olefin (16) and the epoxide (17) are novel and useful intermediates for the synthesis of variety of 2-substituted tert-carbinol derivatives represented in Formula I. For example, olefin (16) on treatment with osmium tetroxide (Reaction Scheme G) gives the diol (18), and the primary alcohol in (18) is alkylated with base (e. g., triethylamine) and alkyl halide ($C_1$–$C_4$) to give the useful intermediate (19) The useful epoxide intermediate (17) can be opened with a variety of nucleophiles (Y) such as hydride, azide, thioalkyl and thioaryl (SR'; R'=H, methyl, phenyl), and amine (NR'R'; R'=H, methyl) to give the intermediate (20). The 2-azidomethyl derivative of compound (19) (Y=$N_3$) can also be elaborated to 2-aminomethyl (Y=$NH_2$) and 2-alkylaminomethyl (Y=NR'R') derivatives. Both the intermediates (19 & 20) can then be elaborated to the fully deprotected compounds represented by structure (21) using the methodologies discussed in Reaction Scheme B for the synthesis of (12).

The preferred conditions used for the synthesis of olefin (16) and epoxide (17) are shown in Reaction Scheme H.

Scheme H:
Synthesis of 2-Methyl Carbinol by Epoxide Opening

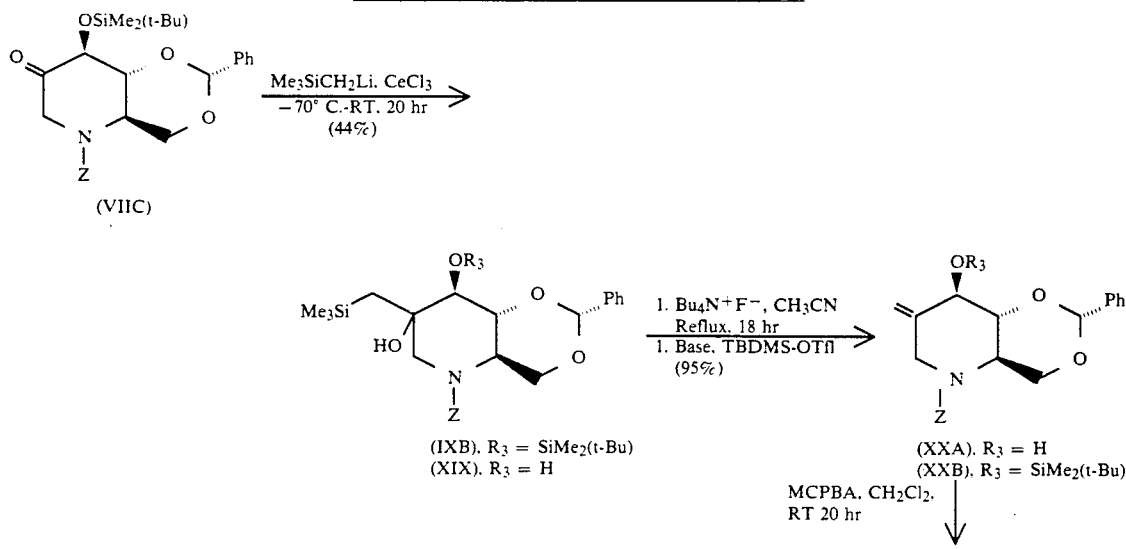

Scheme H:
Synthesis of 2-Methyl Carbinol by Epoxide Opening

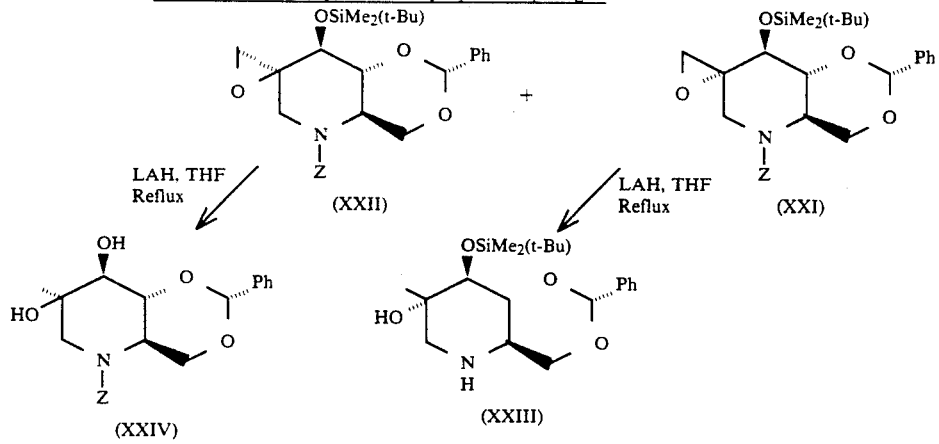

The ketone VIIC is reacted with trimethyl-silylmethyllithium to give the addition product IXB. The acetonitrile solution of compound IXB or XIX is refluxed with a fluoride source such as tetrabutylammonium fluoride to give the novel olefinic intermediate XXA. The hydroxyl group at C-3 in XXA is reprotected using trialkylsilyl (e.g., tert-butyldimethylsilyl) to give the novel olefin XXB. Epoxidation of the olefin (XXB) using 3-chloroperbenzoic acid gives the diastereomeric mixture of epoxides (XXI & XXII) in ratio of 20/80. The lithium aluminum hydride reduction of the epoxides XXI & XXII gives the 2-methyl-tert-carbinol derivatives XXIII & XXIV, respectively.

The intermediate (4) of Reaction Scheme A-B can also be used for the synthesis of 3-substituted ether ($R_8 = C_1-C_6$) or 3-substituted tert-carbinol derivatives ($R_7 = R_4$) as shown in Reaction Scheme I. The intermediates VD and VID of Reaction Scheme D are useful substrates for the synthesis of compounds (5) and (22) shown in Reaction Scheme I.

Scheme I:
Generic Synthesis of 3-substituted 1,5-iminosugars

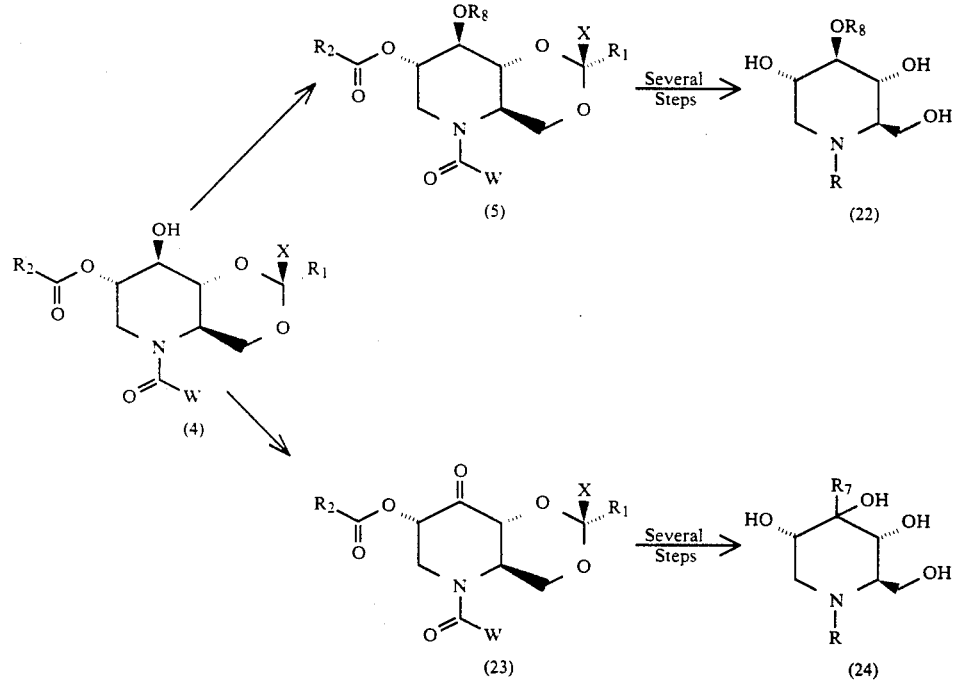

In standard in vitro tests, the novel compounds of the invention were demonstrated to inhibit HIV-1. These tests involved plating of susceptible human host cells which are syncytium-sensitive with and without virus in microculture plates, adding various concentrations of the test compound, incubating the plates for 9 days (during which time infected, non-drug treated control cells are largely or totally destroyed by the virus), and then determining the number of remaining viable cells using a colorimetric endpoint.

Potential use against the AIDS virus also is shown by the inhibitory activity of these compounds against visna virus in a conventional plaque reduction assay. Visna virus, a lentivirus genetically very similar to the AIDS virus, is pathogenic for sheep and goats. See Sonigo et al., *Cell* 42, 369-382 (1985); Haase, *Nature* 322. 130-136 (1986). Inhibition of visna virus replication in vitro as a useful model for human immunodeficiency virus (HIV) and its inhibition by test compounds has been described by Frank et al., *Antimicrobial Agents and Chemotherapy* 31(9), 1369-1374 (1987).

DETAILED DESCRIPTION OF THE INVENTION

The following examples will further illustrate the invention although it will be understood that the invention is not limited to these examples or the details disclosed therein.

EXAMPLE 1

Preparation of 1,5-dideoxy-1,5-[{(phenylmethoxy)carbonyl}imino]--D-glucitol (II)

To a stirred solution of 1-deoxynojirimycin (100 g, 0.61 mol) in saturated aqueous sodium bicarbonate (1000 ml), benzyl chloroformate (95%, 121 g, 0.67 mol) was added dropwise at room temperature After stirring at room temperature for 18 hr, the solution was extracted once with methylene chloride (300 ml) to remove any unreacted benzyl chloroformate. The aqueous layer was then extracted several times with ethyl acetate to give a total of 2.5-3 liters of the extract. The organic layer was then dried ($Na_2SO_4$), filtered and concentrated to give a white solid (98.57 g, 54%), mp 101°-2° C., Anal. calcd. for $C_{14}H_{19}NO_6$: C, 56.56, H, 6.44, N, 4.71. Found: C, 56.33, H, 6.38, N, 4.58. $^1H$ NMR ($CD_3OD$) 7.2-7.4 (m, 5H), 5.15 ( s, 2H), 4.23 (br m, 1H), 4.05 (br d., J=8 Hz, 1H), 3.87 (dd, J=6, 4 Hz, 1H), 3.78-3.85 (m, 2H), 3.70-3.78 (m, 2H), 3.45 (br d, J=8 Hz, 1H).

EXAMPLE 2

Preparation of 1,5-dideoxy-1,5-[{(phenylmethoxy)carbonyl}imino]-4,6-O-(R-phenylmethylene)-D-glucitol (III)

A mixture of (II) (98.5 g, 0.33 mol) , benzaldehyde dimethyl acetal (65.5 g, 0.43 mol) and p-toluenesulfonic acid (1 g) in a round bottom flask was dissolved in dimethylformamide (400 ml). The was connected to a water aspirator and the reaction heated to 60°-65° C. for 4 hr. The reaction mixture w to room temperature and poured into stirred ice-water (1200 ml) containing sodium bicarbonate (14 g). The white solid formed was filtered, washed with cold water and dried. Recrystallization using hexane/ethyl acetate gave III (96.2 g, 54%) as pure white solid, mp 147-48° C., Anal. calcd. for $C_{21}H_{23}NO_6$: C, 65.44, H, 6.02, N, 3.63. Found: C, 65.15, H, 5.93, N, 3.49. $^1H$ NMR ($CD_3OD$) 7.28-7.53 (m, 10H), 5 61 (s, 1H), 5.14 (s, 2H), 4.77 (dd, J =11, 4.6 Hz, 1H), 4.38 (t, J=11 Hz, 1H), 4.16 (dd, J =13.4, 4.2 Hz, 1H), 3.5-3.7 (complex m, 3H), 3.35 (ddd, J=11, 11, 4.6 Hz), 2.97 (dd, J=13.4, 9.3 Hz, 1H).

EXAMPLE 3

Preparation of 1,5-dideoxy-1,5-[{(phenylmethoxy)carbonyl}imino]-4 6-O-(R-phenylmethylene)-D-glucitol, 2-benzoate (IV)

Method A (Using Di-n-butyltin oxide)

A suspension of III (25 g, 64.9 mmol), dibutyltin oxide (98%, 17 g, 66.9 mmol) in toluene (300 ml) was heated to reflux with azeotropic removal of water for 16 hr, whereupon a homogeneous solution resulted. The reaction solution was cooled to room temperature and triethylamine (10.9 ml, 77.5 mmol) and benzoyl chloride (7.7 ml, 67.5 mmol) were added. After stirring at room temperature for 24 hr, the reaction was diluted with aqueous solution of saturated sodium bicarbonate. The aqueous layer was extracted with ethyl acetate (3×800 ml). The combined organic extracts were washed with 1N hydrochloric acid, water and brine. The organic layer was dried ($MgSO_4$) and concentrated and the crude product was purified using column chromatography (silica gel, hexane/ethyl acetate 7/3) to give IV (21.52 g, 68%), DSC (mp) 120° C., Anal. calcd. for $C_{28}H_{27}$: C, 68.70, H, 5.55, N, 2.86. Found: C, 68.17, H, 5.63, N, 2.75. $^1H$ NMR ($CDCl_3$) 7.96 (d, J=8 Hz, 2H), 7.52 (t, J=8 Hz, 1H), 7.48 (m, 2H), 7.36 (t, J=8 Hz, 2H), 7.30 (complex m, 8H), 5.51 (s, 1H), 5.07 (s, 2H) 5.05 (m, 1H), 4.82 (dd, J=11, 5 Hz, 1H), 4.1(dd, J=11, 10 Hz, 1H), 4.04 (dd, J=14, 3 Hz, 1H), 3.88 (dd, J=8, 6 Hz, 1H), 3.73 (dd, J=10, 8 Hz, 1H), 3.65 (brs, 1H), 3.42 (td, J=10, 5 Hz, 1H), 3.38 (dd, J=14, 7 Hz, 1H).

Method B (Using Tetrabutylammonium iodide)

To a suspension of III (1g, 2.6 mol) in methylene chloride (20 ml), tetrabutylammonium iodide (960 mg, 2.6 mol) was added, whereupon a homogenous solution resulted. Anhydrous potassium carbonate (972 mg, 5.2 mmol) was added to the reaction and was followed by addition of benzoyl chloride ( 0.3. ml, 2.6 mmol). After stirring at room temperature for 48 hr, the reaction mixture was filtered and the residue was washed with more methylene chloride. The combined organic filterates were washed with water and dried ($MgSO_4$). After concentration, the crude(2.38 g) was chromatographed (silica gel, hexane/ethyl acetate 7/3) to give IV (810 mg, 64%) identical to the product of Method A.

EXAMPLE 4

Preparation of 1,5-dideoxy-1,5-[{(phenylmethoxy)carbonyl}imino]-4,6-O-(R-phenylmethylene)-3-O-[(2-(methoxy) ethoxy)}methyl]-D-glucitol, 2-benzoate (VA)

To a homogenous solution of IV (1g, 2.04 mmol) in methylene chloride (20 ml), N,N-diisopropylethylamine (99%, 2 ml, 12.27 mmol) and 2-methoxyethoxymethyl chloride (1.4 ml, 12.27 mmol) were added. After stirring at room temperature for 24 hr, the reaction mixture was diluted with methylene chloride (700 ml) and washed with water and brine. After drying ($MgSO_4$) and filteration, the organic solvent was removed and the crude (1.47 g) chromatographed (silica gel, hexane/ethyl acetate 1/1 ) to give pure VA (1.15 g, 98%), DSC (mp) 109° C., Anal. calcd. for $C_{32}H_{35}NO_9$ $_{0.3}H_2O$: C, 65.92, H, 6.15, N, 2.40. Found: C, 65.81, H, 6.09, N, 2.48.

EXAMPLE 5

Preparation of 1,5-dideoxy-1,5-[((phenylmethoxy) carbonyl}imino]-4,6-O-(R-phenylmethylene)-3-O-[(2-(trimethylsilyl)ethoxy] methyl]-D-glucitol, 2-benzoate (VB)

To a homogenous solution of Iv (35g, 0.07 mol) in methylene chloride (450 ml), N,N-diisopropylethylamine (99%, 100 ml, 0.57 mol) and 2-(trimethylsilyl)-ethoxymethyl chloride (74.2 ml, 0.42 mol) were added. After stirring at room temperature for 24 hr, the reaction mixture was diluted with chloride (700 ml) and washed with water and brine. After drying (MgSO$_4$) and filteration, the organic solvent was removed to give VB (60.8 g) as thick orange liquid and was used in the next step without further purification. 1H NMR (CDCl$_3$) 8.19 (d, J=8Hz, 2H), 7.4–7.8 (complex band, 14H), 5.78 (s, 1H), 5.4 (m, 1H), 5.26 (s, 2H), 5.08 (m, 1H), 5.07 (s, 2H), 4.1–4.35 (complex band, 4H), 3.65–3.9 (complex band, 4H), 0.94 (m, 2H), 0.00 (s, 9H).

EXAMPLE 6

Preparation of
1,5-dideoxy-1,5-[{(phenylmethoxy)carbonyl}imino]-4,6-O-(R-phenylmethylene)-3-O-[{2-{(1,1-dimethylethyl) dimethylsilyl}]-D-glucitol, 2-benzoate (VC)

To a homogenous solution of IV (12g, 24.5 mmol) in methylene chloride (200 ml), N,N-diiisopropylethylamine (99%, 12.6 ml, 73.5 mmol) and trifluoromethanesulfonate (11.3 ml 49 mmol) were added. After stirring at room temperature for 2 hr, the reaction mixture was diluted with methylene chloride (700 ml) and washed with aqueous sodium bicarbonate, water and brine. After drying (MgSO$_4$) and filteration, the organic solvent was removed and the crude (19 g) chromatographed (silica gel, hexane/ethyl acetate 8/2 ) to give VC (14.3 g, 97%) as thick liquid. $^1$H NMR (CDCl$_3$) 8.02 (d, J=8Hz, 2H), 7.57 (t, J=8 Hz, 1H), 7.52 (m, 2H), 7.43 (t, J=8 Hz, 2H), 7.37 (m, 2H), 7.30 (m, 6H), 5.58 (s, 1H), 5.14 (ddd, J=7, 5, 3 Hz, 1H), 5.08 (s, 2H), 4.89 (dd, J=11, 5 Hz, 1H), 4.16 (dd, J=11, 10 Hz, 1H), 4.03 (dd, J=14, 3 Hz, 1H), 3.98 (dd, J =8, 5 Hz, 1H), 3.84 (dd, J=10, 8 Hz, 1H), 3.55 (td, J=10, 5 Hz, 1H), 3.55 (dd, J=14, 7 Hz, 1H), 0.79 (s, 9H), 0.02 (s, 3H), 00.0 (s, 3H). ;

EXAMPLE 7

Preparation of
1,5-dideoxy-1,5-[{(phenylmethoxy)-carbonyl}imino]-4 6-O-(R-phenylmethylene)-3-0-methyl-D-glucitol, 2-benzoate (VD)

To a homogenous solution of IV (1.08 g, 1.82 mmol) in dimethylacetamide (20 ml) at 0° C., sodium hydride (182 mg, 60% dispersion in mineral oil, 4.55 mmol) was added. After stirring for 20 min, iodomethane (570 μl, 9.1 mmol) was injected in and the mixture was stirred for 4 hr. The reaction was quenched with drops of acetic acid and diluted with water (100 ml). The crude mixture was extracted with methylene chloride (2×300) and the organic layer was washed with brine. After drying (MgSO$_4$) and filteration, the organic solvent was removed and the crude (1.18 g) chromatographed (silica gel, hexane/ethyl acetate 1/1) to give VD (410 mg, 45%) as white solid, DSC (mp) 130° C., Anal for C$_{29}$H$_{29}$NO$_7$ 0.2H$_2$O: C, 68.68, H, 5.84, N, 2.76 Found C, 68.60, H, 5.89, N, 2.72.

EXAMPLE 8

Preparation of 1,5-dideoxy-1,5[{(phenylmethoxy)carbonyl)imino]4,6-O-(R-phenylmethylene)-3-O-[{2-(methoxy) ethoxy} methyl]-D-glucitol (VIA)

To a solution of VA (12.91 g, 22 mmol) in dioxane (400 ml) and tetrabutylammonium hydroxide (30 ml of 40% aqueous solution diluted to 200 ml) was added. After stirring at room temperature for 5 hr, the reaction was neutralized with 1N HCl and concentrated to remove dioxane. The reaction mixture was extracted with methylene chloride and the organic layer was washed with brine. After drying (MgSO$_4$) and filteration, the solvent was removed and the crude (17.7 g) was chromatographed (silica gel, hexane/ethyl acetate 1/1) to give pure VIA (28.2 g, 93%), DSC (mp) 101° C., Anal. calcd. for C$_{25}$H$_{31}$NO$_8$: C, 63.41, H, 6.60, N, 2 96. Found: C, 63.65, H, 6.68, N, 2.95.

EXAMPLE 9

Preparation of 1,5-dideoxy-1,5-[{(phenylmethoxy) carbonyl}imino]-4,6-O-(R-phenylnethylene)-3-O-[(2-(trimethylsilyl)ethoxy} methyl]-D-glucitol (VIB)

The crude VB (60 g) as obtained above was dissolved in dioxane (500 ml) and tetrabutylammonium hydroxide (150 ml of 40% aqueous solution diluted to 500 ml) was added. After stirring at room temperature for 72 hr, the reaction was neutralized with 1N HCl and concentrated to remove dioxane. The reaction mixture was extracted with methylene chloride (3×800 ml) and the organic layer was washed with brine. After drying (MgSO$_4$) and filteration, the solvent was removed and the crude (90 g) was chromatographed (silica gel, hexane/ethyl acetate 8/2) to give pure VIB (28.2 g, 82% based on 2 steps from IV), DSC (mp)108° C.; Anal. calcd. for C$_{27}$H$_{37}$NO$_7$Si: C, 62.89, H, 7.23, N, 2.72. Found: C, 62.50, H, 7.23, N, 2.65.

EXAMPLE 10

Preparation of 1,5-dideoxy-1,5-[{(phenylmethoxy) carbonyl}iminoi]-4,6-O-(R-phenylmethylene)-3-O-[{2-{(1,1-dimethylethyl)dimethylsilyl}]-D-glucitol (VIC)

The crude VC (660 mg, 1.02 mmol) as obtained above was dissolved in dioxane (20 ml) and tetrabutylammonium hydroxide (1.3 ml of 40% aqueous solution diluted to 10 ml) was added. After stirring at room temperature for 16 hr, the reaction was neutralized with 1N HCl and concentrated to remove dioxane. The reaction mixture was extracted with methylene chloride and the organic layer was washed with brine. After drying (MgSO$_4$) and filteration, the solvent was removed and the crude (560 mg) was chromatographed (silica gel, hexane/ethyl acetate 8/2 ) to give VC (160 mg, and VIC (130 mg, 26%). $^1$H NMR (DMSO-D$_6$) 7.3–7.45 (complex band, 10H), 5.6 (s, 1H), 5.27 (d, J=5.2 Hz, 1H, exchanges with D$_2$O), 5.07 (s, 2H), 4.61 (dd, J=11 & 4.3 Hz, 1H), 4.2 (t, J=10.5 Hz, 1H), 3.82 (dd, J=13.2 & 4 Hz, 1H), 3.64 (dd, J=10 & 8.5 Hz, 1H), 3.51 (dd, J=8.5 & 6.2 Hz, 1H), 3.41 ( complex band, 1H), 3.31 (ddd, J=10.2, 10.2 & 4.5 Hz, 1H), 3.04 (dd, J=13.2 & 8.8 Hz, 1H), 0.78 (s, 9H), 0.00 (s, 6H).

EXAMPLE 11

Preparation of
1,5-dideoxy-1,5-[{(pnenylmethoxy)-carbonyl}imino]-4,6-O-(R-phenylmethylene)-3-O-methyl-D-glucitol (VID) :

To a solution of VD (360 mg, 0.72 mmol) in dioxane (10 ml), tetrabutylammonium hydroxide (1.4 ml of 40% aqueous solution diluted to 7 ml) was added. After stirring at room temperature for 16 hr, the reaction was neutralized with 1N HCl and concentrated to remove dioxane The reaction mixture was extracted with methylene chloride and the organic layer was washed with aqueous sodium bicarbonate and brine. After drying (MgSO$_4$) and filtration, the solvent was removed and the crude (270 mg) was chromatographed (silica gel, hexane/ethyl acetate 1/1) to give VID (210 mg, 73%).

$^1$H NMR (CDCl$_3$) 7.47 (m, 2H), 7.27–7.39 (complex band, 8H), 5.54 (s, 1H), 5.12 (d, J=12 Hz, 1H), 5.07(d, J=12 Hz, 1H), 4.82 (dd, J=12& 5 Hz, 1H), 4.39 (t, J=10 Hz, 1H), 4.22 (dd, J=13 & 5 Hz, 1H), 3.71 (t, J=10 Hz, 1H), 3.62 (s, 3H), 3.60 (complex band, 1H), 3.31 (ddd, J=10, 10 & 5 Hz, 1H), 3.23 (t, J=9 Hz, 1H), 2.94 (broad s, 1H), 2.87 (dd, J=13 & 9 Hz, 1H).

EXAMPLE 12

Preparation of 1,5-dideoxy-1,5-[{(phenylmethoxy) carbonyl}imino]-4,6-O-(R-phenylmethylene)-3-O-[{2-(methoxy)ethoxy}methyl]-L-sorbose (VIIA)

To a cold solution of dimethyl sulfoxide (2.55 ml, 35.5 mmol) in methylene chloride (40 ml) at −70° C., trifluoroacetic anhydride (3.8 ml, 26.62 mmol) in methylene chloride (40 ml) was added over 15–20 min. The reaction mixture was stirred for 10 min and then a solution of VIA (8.4 g, 17.74 mmol) in methylene chloride (200 ml) was added over 20 min. The reaction temperature was allowed to rise to −20° C. over 90 min and then stirred at −30° C. for additional 2 hr. Reaction mixture was recooled (−70° C.) and triethylamine (8 ml) was added over 10 min. After stirring at −70° C. for 1 hr, the cold bath was removed and the reaction was stirred for 2 hr. The reaction solution was diluted with methylene chloride and washed with water. After drying over MgSO$_4$, the organic fractions were filtered and concentrated. The crude liquid (9.45 g) was chromatographed (silica gel, hexane/ethyl acetate 1/1) to give VIIA (7.5 g, 89%) as pure white solid, DSC (mp)116° C.; Anal. calcd. for C$_{25}$H$_{29}$NO$_8$. 0.25 H$_2$O: C, 63.08, H, 6.25, N, 2.94. Found: C, 63.03, H, 6.22, N, 2.90.

EXAMPLE 13

Preparation of 1,5-dideoxy-1,5-[{(phenylmethoxy)carbonyl}imino]-4,6-O-(R-phenylmethylene)-3-O-[{2-(trimethylsilyl)ethoxy) methyl]-L-sorbose.(VIIB)

To a cold solution of dimethyl sulfoxide (6.58 ml, 0.092 mol) in methylene chloride (30 ml) at −70° C., trifluoroacetic anhydride (10.1 ml 0.071 mol) in methylene chloride (30 ml) was added over 15–20 min. The reaction mixture was stirred for 20 min and then a solution of VIB (22.75 g, 0.046 mol) in methylene chloride (200 ml) was added over 45 min. The reaction temperature was allowed to rise to −20° C. over 90 min and then stirred at −20° C. for an additional 4 hr. The reaction mixture was recooled (−70° C.) and triethylamine (20 ml) was added over 10 min. After stirring at −70° C. for 45 min, the cold bath was removed and the reaction was stirred for 1 hr. The reaction solution was diluted with methylene chloride and washed with water. After drying over MgSO$_4$, the organic were filtered and concentrated. The crude liquid (39 g) was chromatographed (silica gel, hexane/ethyl acetate 75/25) to give VIIB (22.1 g, 97%) as white solid, mp 112°–114° C.; Anal. calcd. for C$_{27}$H$_{35}$NO$_7$Si.1H$_2$O: C, 61.0, H, 7.01, N, 2.63. Found: C, 61.19 H, 7.01, N, 2.72.

EXAMPLE 14

Preparation of 1,5-dideoxy-1,5-[{(phenylmethoxy) carbonyl}imino]-4,6-O-(R-phenylmethylene)-3-O-[{2-[{(1,1-dimethylethyl) dimethylsilyl}]-L-sorbose (VIIC)

To a cold solution of dimethyl sulfoxide (0.37 ml, 5.21 mol) in methylene chloride (5 ml) at −70° C., trifluoroacetic anhydride (0.57 ml 4.04 mmol) in methylene chloride (5 ml) was added over 10 min. The reaction mixture was stirred for 10 min and then a solution of VIC (1.3 g, 2.6 mmol) in methylene chloride (20 ml) was added over 15 min. The reaction temperature was allowed to rise to −30° C. over 4 hr and then stirred at −40° C. for additional 1 hr. Reaction mixture was recooled (−70° C.) and triethylamine (1 ml) was added over 10 min. After stirring at −70° C. for 1 hr, the cold bath was removed and and the reaction was stirred for 1 hr. The reaction solution was diluted methylene chloride and washed with water. After drying over MgSO$_4$, the organic fractions were filter concentrated. The crude compound (1.48 g) was c (silica gel, hexane/ethyl acetate 8/2) to give VIIC (0.99 g, 76%). $^1$H NMR (CDCl$_3$) 7.47 (m, 2H), 7.32 (m, 8H), 5.56 (s, 1H), 5.12 (d, J=12 Hz, 1H), 5.06 (d, J=12 Hz, 1H), 4.77 (dd, J=11, 5 Hz, 1H), 4.25 (d, J=10 Hz, 1H), 4.18 ( d, J=18 Hz, 1H), 4.14 (dd, J=11, 10 Hz, 1H), 4.07 (d, J=18 Hz, 1H), 3.93(t, J=10 Hz, 1H), 3.70 (td, =10, 5 Hz, 1H), 0.86 (s, 9H), 0.11 (s, 3H), 0.0 (s, 3H).

EXAMPLE 15

Preparation of 1,5-dideoxy-1,5-[{(phenylmethoxy)-carbonyl}imino]-4,6,-O-(R-phenylmethylene)-3-O-methyl-L-sorbose (VIID):

To a cold solution of dimethyl sulfoxide (75 μl, 1.06 mol) in methylene chloride (5 ml) at −70° C., trifluoroacetic anhydride (112μl, 0.79 mmol) in methylene chloride (5 ml) was added over 5 min. The reaction mixture was stirred for min and then a solution of VID (210 mg, 0.53 mmol) in methylene chloride (5 ml) was added over 10 min. The reaction temperature was allowed to rise to −30° C. over 3 hr and then stirred at −30° C. for an additional 4 hr. Reaction mixture was recooled (−70° C.) and triethylamine (0.4 ml) was added over 10 min. After stirring at −70° C. for 1 hr, the cold bath was removed a reaction was stirred for 1 hr, the cold bath was removed and the reaction was stirred for 1 hr. The reaction solution was diluted with methylene chloride and washed with water. After drying over MgSO$_4$, the organic fractions were filtered and concentrated. The crude compound (260 mg) was chromatographed (silica gel, hexane/ethyl acetate 6/4) to give VIID (190 mg, 91%). $^1$H NMR (CDCl$_3$) 7.51 (m, 2H), 7.36 (m, 8H), 5.61 (s, 1H), 5.17 (d, J=12 Hz, 1H), 5.10 (d, J=12 Hz, 1H), 4.82 (dd, J=11, 5 Hz, 1H), 4.25 (d, J=16 Hz, 1H), 4.21 (dd, J=11, 10 Hz, 1H), 4.11 (d, J - 16 Hz 1H), 4.06 (t, J=10 Hz, 1H), 3.96 (d, J=10 Hz, 1H), 3.77 (td,=10, 5 Hz, 1H), 3.64 (s, 3H).

EXAMPLE 16

Preparation of 1,5-dideoxy-2-C-methyl-1,5-[{(phenylmethoxy) carbonyl}imino]-4,6 -O-(R-phenylmethylene)-3-O-[{2-[{(1,1-dimethylethyl) dimethylsilyl}]-D-mannitol (VIIIB)

To a cold solution of VIIC (620 mg, 1.25 mmol) in tetrahydrofuran (15 ml) at −70° C., methyl magnesium bromide (1.25 ml, 3M in Et$_2$O, 3.75 mmol) Was added over 10 min. The reaction mixture was allowed to warm to −30° C. over 3hr. After stirring at −20° to −30° C. for 2hr, the reaction was quenched by adding saturated aqueous ammonium chloride and extracted with ethyl acetate. The organic layer was washed with brine and dried (MgSO$_4$), filtered and concentrated. The crude product (600 mg) was chromatographed (silica gel, hexane/ethyl acetate 8/2) to give pure VIIIB (440 mg, 67%). 1H NMR (CDCl₃) 7.49 (m, 2H), 7.39 (m, 8H), 5.54 (s,1H), 5.17 (d, J=12 Hz, 1H), 5.13 (d, J=12 HZ, 1H), 4.72 (dd, J=12, 5 Hz; 1H), 4.66 (dd, J=12, 10 Hz, 1H), 4.28 (d, J=14 Hz, 1H), 3.9 (dd, J=10, 8 Hz, 1H), 3.55 (d, J=8 Hz, 1H), 3.25 (d, J=10, 5 Hz, 1H), 2.83 (dd, J=14, 2 Hz, 1H), 2.73 (d, J=2 Hz, 1H), 1.24 (s, 3H), 0.87 (s, 9H), 0.05 (s, 3H), −0.05 (s, 3H).

EXAMPLE 17

Synthesis of phenylmethyl 8β-[{(1,1-dimethylethyl) dimethylsilyl)oxy]hexahydro-7-hydroxy-2R, 2α-phenyl-7-[(trimethylsilyl)methyl]5H-4aα, 8aβ-1, 3-dioxino[5,4-b]pyridine-5-carboxylate (IXB)

The cerium chloride (1.5g, 6 mmol) dried under vacuum (0.1 mm Hg) with stirring at 140° C. for 18 hr. After cooling to approx. 20° C., dry#tetrahydrofuran (50 ml) was added and the mixture was stirred under argon for 2 hr. The reaction mixture was cooled to −78° C. and trimethylsilylmethyllithium (12 ml 1M solution in pentane, 12 mmol) was added to the reaction flask over 10 min. After stirring for 1 hr, a solution of VIIC (1.35 g, 2.7 mmol) in THF (35 ml) added over 20 min. The bath temperature was allowed rise to −10° C. over 4 hrs and stirred at −10° C. for 18 hrs. The reaction mixture was quenched with ethylenediamine (1.5 ml), stirred for 40 min and then diluted with ethyl acetate. The organic layer was separated and washed with aqueous potassium carbonate and brine. After drying the organic layer over MgSO₄, the solvent was removed and the crude product (1.82 g) chromatographed (silica gel, hexane/ethyl acetate 8/2) to give IXB (680 mg, 43%). ¹H NMR (CDCl₃) 7.25-7.57 (complex band, 10H), 5.52 (s, 1H), 5.14 (d, J=12 Hz, 1H), 5.10 (d, J=12 Hz, 1H), 4.69 (m, 2H), 4.42 (d, J=14 Hz, 1H), 3.85 (dd, J=10, 8 HZ, 1H), 3.48 (d, J=8 Hz, 1H), 3.24 (distorted q, J=9 Hz, 1H), 2.73 (broad d, J=14 Hz, 1H), 2.65 (broad s, 1H), 1.4 ( d, J=15 Hz, 1H), 0.86 (s, 9H), 0.62 (d, J=15 Hz, 1H), 0.06 (s, 9H), 0.04 (s, 3H), −0.07 (s, 3H).

EXAMPLE 18

Preparation of 1,5-dideoxy-2-C-methyl-1,5-[{(phenylmethoxy) carbonyl)imino]-4,6-O-(R-phenylmethylene)-3-O-[{2-(methoxy)ethoxy} methyl]-D-glucitol (XA) and 1,5-dideoxy-2-C-methyl-1,5-[{(phenylmethoxy)carbonyl}imino]-4,6-O-(R-phenylmethylene)-3-O-[2-(methoxy)ethoxy)} methyl}-mannitol XB To a cold solution of VIIA (4.92 g, 10.43 mmol) in tetrahydrofuran (120 ml) at −70° C., methyl magnesium bromide (10.5 ml, 3M in Et₂O, 31.3 mmol) was added over 10 min. The reaction mixture was stirred at −70° C. for 2 hr and then allowed to warm to −30° C. over 2hr. After stirring at −30° C. for 4 hr, the reaction was quenched by adding saturated aqueous ammonium chloride (700 ml) and extracted with ethyl acetate. The organic layer was washed with brine and dried (MgSO₄), filtered and concentrated. The crude (5.4 g) was chromatographed (silica gel, hexane/ethyl acetate 1/1) to give XA (1.08 g, 21%) and XB (2.2 g, 43.3%).

XA: mp 75°-76° C.; Anal calcd. for C₂₆H₃₃NO₈: C,64.05, H, 6.82, N, 2.87 Found C, 63.74, H, 6.92, N, 2.80; ¹H NMR (CDCl₃) 7.48 (m, 2H), 7.37 (m, 8H) 5.53 (s,1H), 5.11 (d, J=12 Hz, 1H), 5.06 (d, J=12 Hz, 1H), 4.87 (d, J=5 Hz, 1H), 4.85 (d, J=5Hz, 1H) 4.83 (dd, J=12, 5 Hz, 1H), 4.52 (dd, J=12, 11 Hz, 1H), 4.35 (broad s, 1H), 4.18 (d, J=14 Hz, 1H), 3.90 (m, 1H), 3.68 (m, 1H), 3.63 (dd, J=9.5, 9 Hz, 1H), 3.56 (d, J=9 Hz, 1H), 3.53 (m, 2H), 3.37 (s, 3H), 3.126 (ddd, J=11, 9.5, 5 HZ, 1H), 2.79 (d, J=14 Hz, 1H) 1.23 (s, 3H). XB: Anal calcd. for C₂₆H₃₃NO₈ 0.8H₂O: C,62.21, H, 6.95, N, 2.79 Found C, 62.31, H, 6.71, N, 2.74; ¹H NMR (CDCl₃) 7.48 (m, 2H), 7.37 (m, 8H), 5.54 (s,1H), 5.13 (d, J=12 Hz, 1H), 5.09 (d, J=12 Hz, 1H), 5.06 (d, J=7 Hz, 1H)., 4.83 (d, J=7Hz, 1H), 4.74 (dd, J=12, 5 Hz, 1H), 4.60 (dd, J=12, 10 Hz, 1H), 4.21 (d, J=14 Hz, 1H), 4.08 (dd, J=10, 9 Hz, 1H), 3.76 (m, 1H), 3.68 (m, 1H), 3.55 (d, J=9 Hz, 1H), 3.36 (m, 2H), 3.3i (s, 3H), 3.23 (ddd, J=11, 10, 5 Hz, 1H), 2.8 (d, J=14 Hz, 1H), 2.49 (broad s, 1H), 1.27 (s, 3H).

EXAMPLE 19

Preparation of 1,5-dideoxy-2-C-methyl-1,5-[{(phenylmethoxy) carbonyl)imino]-4,6-O-(R-phenylmethylene)-3-O-[{2-(trimethylsilyl)ethoxy} methyl]-D glucitol (XIA) and 1,5-dideoxy-2-C-methyl-1,5-[{(phenylmethoxy)carbonyl}imino]-4,6-O-(R-phenylmethylene)-3-O-[{2-(trimethylsilyl)ethoxy} methyl]-D-mannitol (XIB)

To a cold solution of VIIB (720 mg, 1.47 mmol) in tetrahydrofuran (25 ml) at −70° C., methyl magnesium bromide (1.5 ml, 3M in Et₂O, 4.41 mmol) was added over 10 min. The reaction mixture was allowed to warm to −30° C. over 3hr. After stirring at −20° to −30° C. for 4hr, the reaction was quenched by adding saturated aqueous ammonium chloride and extracted with ethyl acetate (2×150 ml). The organic layer was washed with brine and dried (MgSO₄), filtered and concentrated. The crude (920 mg) was chromatographed (silica gel, hexane/ethyl acetate 75/25) to give pure XIA (530 mg, 68%) and XIB (42 mg, 5%). X1A: Anal calcd. for C₂₈H₃₉NO₇Si.0.5H₂O: C,62.43, H, 7.48, N, 2.6 Found C, 62.34, H, 7.34, N, 2.56; ¹H NMR (CDCl₃) 7.48 (m, 2H), 7.37 (m, 8H) 5.54 (s,1H), 5.10 (d, J=12 Hz, 1H), 5.05 (d, J=12 Hz, 1H), 4.88 (d, J=7 Hz, 1H), 4.82 (dd, J=11.5, 4 HZ, 1H), 4.68 (d, J=7Hz, 1H), 4.52 (br.t, J=11.5, 11 Hz, 1H), 4.43 (s, 1H), 4.19 (d, J=14 Hz, 1H), 3.86 (m, 1H), 3.63 (dd, J =10, 9 Hz, 1H), 3.56 (m, 1H), 3.44 (d, J=9 Hz, 1H), 3.25 (td, J=10, 4 Hz, 1H), 2.77 (d, J=14 Hz, 1H), 1.21 (s, 3H). 0.94 (m, 2H), 0 (s, 9H). X1B: 1H NMR (CDCl₃) 7.48 (m, 2H), 7.37 (m, 8H), 5.57 (s,1H), 5.16 (d, J=12 Hz, 1H), 5.11 (d, J=12 Hz, 1H), 5.02 (d, J=7 Hz, 1H), 4.83 (d, J=7Hz, 1H), 4.74 (dd, J=11.5, 4.7 Hz, 1H), 4.62 (br.t, J=11.5, 10.2 Hz, 1H), 4.24 (d, J=14 Hz, 1H), 4.10 (dd, J=9.9, 8.8 Hz, 1H), 3.76 (m, 1H), 3.56 (m, 1H), 3 54 (m, 1H), 3.25 (td, J=10, 4.7 Hz, 1H), 2.83 (d J=14, 1.9 Hz, 1H), 2.37 (d, J=1.9 Hz, 1H), 1.3 (s, 3H). 0.91 (m, 2H), 0 (s, 9H).

EXAMPLE 20

Preparation of 1,5-dideoxy-2-C-methyl-1,5-[{(phenylmethoxy) carbonyl}imino]-4,6-O-(R-phenylmethylene)-3-O-methyl-D-glucitol and 1,5-dideoxy-2-C-methyl-1,5-[{(phenylmethoxy) carbonyl}imino]-4,6-O-(R-phenylmethylene)-3-O-methyl-D-mannitol XIIB:

To a cold solution of VIID (193 mg, 0.5 mmol) in tetrahydrofuran (10 ml) at −70° C., methyl magnesium bromide (0.5 ml, 3M in Et₂O, 1.5 mmol) was added over 10 min. The reaction mixture was allowed to warm to −30° C. over 2hr. After stirring at −20° to −30° C. for 4hr, the reaction was quenched by adding saturated aqueous ammonium chloride and extracted with ethyl acetate (50 ml). The organic layer was washed with brine and dried (MgSO$_4$), filtered and concentrated. The crude (190 mg) was chromatographed (silica gel, hexane/ethyl acetate 1/1) to give pure XIIA (111 mg, 54%) and XIIB (7.1 mg, 4%). XIIA. Anal calcd. for C$_{23}$H$_{27}$NO$_6$.0.2H$_2$O: C,66.24, H, 6.62, N, 3.32 Found C, 66.12, H, 7.17, N, 3.05; $^1$H NMR (CDCl$_3$) 7.49 (m, 2H), 7.36 (m, 8H) 5.57 (s,1H), 5.12 (d, J=12 Hz, 1H), 5.07 (d, J=12 Hz, 1H), 4.84 (dd, J −12, 5 Hz, 1H) 4.50 (dd J=12, 10 Hz 1H) 4.10 (d J=13 HZ, 1H), 3.69 (t, J=10 Hz, 1H), 3.66 (s, 3H), 3.31 (td, J=10, 5 Hz, 1H), 3.26 (d, J=10 Hz, 1H), 2.84 (d, J=13 HZ, 1H), 2.25 (s, 1H), 1.22 (s, 3H). XIIB. Anal calcd. for C$_{23}$H$_{27}$NO$_6$. 0: C,66.81, H, 6.58, N, 3.39 Found C, 66.91, H, 6.90, N, 2.94; $^1$H NMR (CDCl$_3$) 7.25–7.5 (m, 10H), 5.60 (s, 1H), 5.14 (d, J=12 Hz, 1H), 5.09 (d, J=12 Hz, 1H), 4.73 (dd, J=11, 5 Hz, 1H), 4.62 (dd, J=11, 10.6 Hz, 1H), 4.22 (d, J=14 HZ, 1H), 4.06 (dd, J=10, 8.7 Hz, 1H), 3.66 (s, 3H), 3.21 (td, J =10, 4.6 Hz, 1H), 3.08 (d, J=8.7 Hz, 1H), 2.79 (dd, J =14,1.8 Hz, 1H), 2.36 (d, J=1.8 Hz, 1H), 1.26 (s, 3H).

EXAMPLE 21

Preparation of 1,5-dideoxy-2-C-methyl-1,5-[{phenylmethoxy)carbonyl}imino]-4,6-O-(R-phenylmethylene)-D-glucitol (XIII)

To a homogenous solution of XIA (7.8 g. 14.75 mmol) in tetrahydofuran (150 ml), tetrabutylammonium fluoride (88 ml, 1M solution in tetrahydofuran, 88 mmol) was added. After stirring at room temperature for 25 min, the solvent was removed and the residue dried under vacuum for 4 hr. The dried product was in 1,3-dimethyl-3, 4,5,6-tetrahydro-2(1H)-pyrimidinone (DMPU) (50 ml) and molecular sieves (4A°, pre-dried, 5g) were added. The reaction mixture was heated at 80° C. for 18 hr, cooled to room temperature and diluted with Et$_2$O (1000 ml). The ethereal layer was separated, washed with water, dried (MgSO$_4$) and concentrated. The crude product (13.6 g) was chromatographed (silica gel, hexane/ethyl acetate 1/1) to give XIII (3.83 g, 65%) as pure white solid, mp 104°–6° C.; Anal. calcd. for C$_{22}$H$_{25}$NO$_6$ 0.3H$_2$O: C, 65.27, H, 6.37, N, 3.46. Found: C, 65.22, H, 6.29, N, 3.42. $^1$H NMR (CDCl$_3$) 7.48 (m, 2H), 7.37 (m, 8H), 5.51 (s,1H), 5.11 (d, J=12 Hz, 1H), 5.06 (d, J=12 Hz, 1H), 4.81 (dd. J=12, 5 Hz, 1H), ,4.44 (dd, J=12, 10 Hz, 1H), 4.06 (d, J=14 Hz, 1H), 3.59 (d, J=9 Hz, 1H, 3.51 (dd, J=10, 9 Hz, 1H), 3.23 (td, J =10, 5 Hz, 1H), 2.73 (d, J=14 Hz, 1H), 2.98 (broad s, 1H), 2.58 (broad s, 1H), 1.2 (s, 3H).

EXAMPLE 22

Preparation of 1,5-dideoxy-1,5-imino-2-C-methyl-4,6-O-(R-phenylmethylene)-D-glucitol (XIV)

To a solution of XIII (3 g, 7.5 mmol) in methanol (200 ml) in a Fischer-Porter bottle, 10% Pd on C (375 mg) was added. The bottle was sealed, purged with nitrogen, purged with hydrogen and then pressurized to 60 psi hydrogen pressure. After agitating at room temperature for 70 min, the reaction was vented to remove hydrogen. The catalyst was filtered and the residue washed with more methanol. The combined organic filterates were concentrated and the crude product was chromatographed (silica gel, methylene chloride / methanol/ 30% aqueous ammonium hydroxide 90/10/1) to give pure XIV (1.68 g, 84%) as white solid.

Anal. calcd. for C$_{14}$H$_{19}$NO$_4$ 0.25 H$_2$O: C, 62.32, H, 7.28, N, 5.19. Found: C, 62.28, H, 7.44, N, 5.106

EXAMPLE 23

Synthesis of 1,5-imino-1,5-dideoxy-2-C-methyl-D-glucitol (XV)

Method A (Using Transfer hydrogenation)

To a clear solution of XIV (550 mg, 2.07 mmol) in ethanol (20 ml) and cyclohexene (40 ml), 20% Pd(OH)$_2$ on C (500 mg) was added. After refluxing the mixture for 6 added. The mixture was refluxed for 18 hr and additional amounts of catalyst (200 mg) and cyclohexene (80 ml) were added. After refluxing for an additional 24 hrs, the reaction mixture was cooled and filtered. The residue was washed with methanol (300 ml) and the filterate was concentrated to give the residue (620 mg). The residue was subjected to chromatography (silica gel, 90/10/1 and then methylene chloride/methanol/30% ammonium hydroxide 50/50/2.5) and recovered starting material XIV (90 mg, 16%) and XV (285 mg, 73%) as pure white solid. DSC (mp) 214°–16° C. Anal. calcd. for C$_7$H$_{15}$NO$_4$0.1 H$_2$O: C, 46.97, H, 8.56, N, 7.82. Found: C, 46.87, H, 8.62, N, 7.79.

Method B (Using sodium/liq. ammonia)

The compound XIV (180 mg, 0.68 mmol) was dissolved in liquid ammonia (20 ml) at −70° C. and was reduced by adding small pieces of sodium metal. The reaction mixture was stirred for 20 mins at −60° C. The cold bath was removed and the excess ammonia was allowed to escape. The white residue was quenched with water and the solution was passed thru an ion-exchange column (Amberlite IRA 400, OH). The basic fractions were collected and concentrated. The product (190 mg) was purified by chromatographed a Method A to give XV (55 mg, 45%) identical to the of Method A.

EXAMPLE 24

Synthesis of 1,5-Butylimino-1,5-dideoxy-2-C-methyl-D-glucitol (XVIA)

To a solution of XV (170 mg, 0.96mmol) and butyraldehyde (150 mg, 2.1 mmol) in methanol (12 ml), water (3ml) and tetrahydrofuran (6 ml) in a Fischer-Porter bottle, 5% Pd on C (35 mg) was added. The bottle was sealed, purged with nitrogen, purged with hydrogen and then pressurized to 5 psi h pressure. After agitating at room temperature for 70 hr, the reaction was vented to remove hydrogen. The catalyst was filtered and the residue washed with more methanol. The combined organic filterates were concentrated and the crude product (260 mg) was chromatographed (silica gel, methylene chloride/methanol/30% ammonium hydroxide 85/15/1.5) to give XVIA (188 mg, 84%). mp 68°–70° C. , Anal. calcd. for C$_{11}$H$_{23}$NO$_4$0.25 H$_2$O: C, 55.56, H, 9.96, N, 5.89. Found: C, 55.58, H, 9.86, N, 5.79.

EXAMPLE 25

Synthesis of 1,5-(3-phenylpropylimino)-1,5-dideoxy-2-C-methyl-D-glucitol (XVIB)

The type reaction of Example 24 was repeated using XV (130 mg, 0.73 mmol) and 3-phenylpropionaldehyde (130 mg, 0.97 mmol), 5% pd on C (30 mg) in methanol (12 ml), water (3 ml) and tetrahydrofuran (3 ml). The crude (220 mg) obtained after work up was purified on column (silica gel, methylene chloride/methanol/30% ammonium hydroxide 75/25/1) to give pure XVIB (140 mg, 65%), DSC (mp) 94° C., Anal. calcd. for $C_{16}H_{25}NO_4 \cdot 0.4H_2O$: C, 63.51, H, 8.59, N, 4.63. Found: C, 63.56 H, 8.36, N, 4.66.

EXAMPLE 26

Synthesis of 1,5-(2-ethylbutylimino)-1,5-dideoxy-2-C-methyl-D-glucitol (XVIC)

The type reaction of Example 24 was repeated using XV (130 mg, 0.73 mmol) and 2-ethylbutyraldehyde (130 mg. 1.3 mmol), 5% pd on C (30 mg) in methanol (12 ml), water (3 ml) and tetrahydrofuran (3 ml). The crude product (220 mg) obtained after work up was chromatographically purified on a column (silica gel, methylene chloride/methanol/30% ammonium hydroxide 75/25/1) to give pure XVIC (70 mg, 37%), mp 78°–80° C., Anal. calcd. for $C_{13}H_{27}NO_4 \cdot 0.3H_2O$: C, 58.53, H, 10.43, N, 5.25. Found: C, 58.64, H, 10.15, N, 5.35

EXAMPLE 27

Synthesis of 1,5-dideoxy-2-C-methyl-1,5-[(1-oxabutyl)imino]-D-glucitol, 6-butanoate (XVIIA)

A solution of XV (35 mg, 0.2 mmol) in butyric anhydride (3 ml) was stirred at room temperature. After 28 hr, the solvent was removed under argon at room temperature and the crude liquid was passed through a short column (silica gel, methylene chloride/methanol/ammonium hydroxide 90/10/1) to give XVIIA (29 mg, 46%), $^1$H NMR (CD$_3$OD) 5.08 (broad dd, J=10, 4 Hz, 1 H), 4.81 (dd, J=12, 10 Hz, 1H), 4.64 (dd, J=12, 10 Hz, 1H), 4.36 (broad D, J=10 Hz, 1H), 4.29 (d, J=14 Hz, 1H), 4.12 (dd, J=12, 4 Hz, 1H), 4.06 (dd, J=12, 4 Hz, 1H), 3.82 (dd, J=4, 2 Hz, 2H), 3.47 (s, 2H), 3.46 (d, J=4 Hz, 1H), 3.45 (d, J=4 Hz, 1H), 2.94 (d, J=14 Hz, 1H), 2.56 (ddd, J=15, 8, 6 Hz, , 2.43 (t, J=7 Hz, 1H), 2.36 (ddd, J=15, 8, 1H), 2.28 (t, J=7 Hz, 2H), 2.24 (t, J=7 Hz, , 1.53–1.75 (complex band, 8H), 1.20 (s, 6H), (t, J=7 Hz, 3H), 0.92 (t, J=7 Hz, 3H). It be noted that the integrals to NMR signals are assigned assuming that 1H=one proton signal of one rotamer.

EXAMPLE 28

Synthesis of 1,5-dideoxy-2-C-methyl-1,5-[(1-oxabutyl)imino1-D-glucitol(XVIIB):

To a solution of XV (22 mg, 0.12 mmol) in methanol (0.5 ml), butyric anhydride (0.5 ml) was added and the reaction mixture was stirred at room temperature After 3 hr, the solvent was removed under argon at room temperature and the crude liquid was passed through a short column (silica gel, methylene chloride/methanol/ammonium hydroxide 90/10/1) to give XVIIA (6.9 mg. 10%) and XVIIB (27 mg, 88%). 1H NMR (CD$_3$OD) 4.32 (d, J=14 Hz, 1H), 4.17 (broad dd, J=7, 1.5 Hz, 1H), 4.02 (dd, J=12, 9.5 Hz, 1H), 3.89 (broad t, J=2.4 Hz 1H) 3.81 (dd J=12, 7.4 Hz, 1H), 3.79 (m, 1H), 3.78 (m, 1H), 3.76 (dd, J=12, 6.1 Hz, 1H), 3.63 (dd, J=12, 4.3 Hz, 1H), 3.51 (d, J=14 Hz, 1H), 3.45 (m, 2H), 3.40 (d, J=14 Hz, 1H), 2.92 (d, J=14 Hz, 1H), 2.58 (m, 1H), 2.46 (m, 1H), 2.46 (t, J=7.3 Hz, 2H), 1.67 (m, 4H), 1.18 (s, 6H), 0.97 (t, J=7 Hz, 3H), 0.96 (t, J=7 Hz, 3H). It might be noted that the integrals to NMR signals are assigned assuming that 1H=one proton signal of one rotamer. MS (EI) 247 (M+)

EXAMPLE 29

Synthesis of 1,5-(butylimino)-1,5-dideoxy-2-C-methyl-D-glucitol, (3 and/or 4), 6-perbutanoate (XVIIIA, XVIIIB & XBIIIC)

To a suspension of XVIA (35 mg, 0.15 mmol) in pyridine (3 ml), butyric anhydride (145 μl, 0.89 mmol) was added and the mixture was stirred for 7 days. The solvent was removed under argon at room temperature and the crude (62 mg) was chromatographed (silica gel, hexane/ethyl acetate 1/1) to give XVIIIA (6 mg 9%), XVIIIB (16 mg, 29%) & XVIIIC (9 mg, 16%). XVIIIA $^1$H NMR (CDCl$_3$) 4.99 (t, J=6 Hz, 1H), 4.80 (d, J=6.4 Hz, 1H), 4.25 (dd, J =12, 5 Hz, 1H), 4.21 (d, J=12, 5 Hz, 1H), 3.07 (broad s, 1H), 2.83 (d, J=12 Hz, 1H), 2.82 (m, 1H), 2.64 (m, 1H), 2.54 (m, 1H), 2.2–2.39 (complex band, 7H), 1.53–1.7 (complex band 6H) 1.43 (m 2H) 1.3 (m 2H) 1.22 (s, 3H), 0.88–0.97 (complex band, 12H); MS (Cl, NH$_3$) 444 (M+1).

XVIIIB $^1$H NMR (CDCl$_3$) 4.69 (d, J=7.7 Hz, 1H), 4.43 (dd, J=12.2, 3.8 Hz, 1H), 4.35 (dd, J=12.2, 3.8 Hz, 1H), 3.56 (broad t, J=7.4 Hz, 1H, 2.78 (d, J=11.7 Hz, 1H), 2.71 (m, 1H), 2.58 (td, J=7.4, 3.8 Hz, 1H), 2.49 (m, 1H), 2.28–2.4 (complex band, 4H), 1.61–1.73 (complex band, 4H), 1.43 (m, 2H), 1.3 (m, 2H), 1.22 (s, 3H), 0.88–1 (complex band 9H); MS (Cl, NH$_3$) 374 (M+1) XVIIIC 1H NMR (CDCl$_3$) 4.84 (t, J=7 Hz, 1H), 4.34 (dd, J=12.2, 4 Hz, 1H), 4.20 (dd, J=12.2, 3.9 Hz, 1H), 3.48 (dd, J=7.2, 5.3 Hz, 1H), 2.80 (d, J=11.5 Hz, 1H), 2.71 (m, 1H), 2.68 (m, 1H), 2,53 (m, 1H), 2.25–2.38 (complex band, 4H), 1.62–1.71 (complex band, 4H), 1.42 (m, 2H), 1.32 (m, 2H), 1.28 (s, 3H), 0.88–1 (complex band, 9H); MS (Cl, NH$_3$) 374 (M+1).

EXAMPLE 30

Synthesis of phenylmethyl hexahydro-8β-hydroxy-7-hydroxy-2R, 2α-phenyl-7-[(trimethylsilyl)methyl]-5H-4aα. 8aβ-1,3-dioxino[5,4-b]pyridine-5-carboxylate (XIX)

To a solution of IXB (60mg, 0.1 mmol) in THF (4 ml), tetrabutylammonium fluoride (0.3 ml, 1M solution in THF, 0.3 mmol) was added and the contents were stirred at 20° C. for 18 hr. The reaction mixture was diluted with ethyl acetate and the organic layer was washed with water and brine. After drying (MgSO$_4$), the solvent was removed and the crude product (58 mg) was chromatographed (silica gel, hexane/ethyl acetate 7/3) to give XIX (40 mg, 85%). $^1$H NMR (CDCl$_3$) 7.49 (m, 2H), 7.37 (m, 8H), 5.57 (s, 1H), 5.14 d, J=12 Hz, 1H), 5.10 (d, J=12 Hz, 1H), 4.76 (dd, J=12, 5 Hz, 1H), 4.61 (dd, J=12, 10 Hz, 1H), 4.38 (d, J=14 Hz, 1H), 3.90 (dd, J=10, 8 Hz, 1H), 3.46 (dd, J=8, 2.5 Hz, 1H), 3.22 (td, J=10, 5 Hz, 1H), 2.74 (dd, J=14, 2 Hz, 1H) 2.63 (d J=2.5 Hz 1H) 2.29 (d J=2 Hz, 1H), 1.33 (d, J=15 Hz, 1H), 0.80 (d, J=15 Hz, 1H), 0.07 (s, 9H).

EXAMPLE 31

Synthesis of phenylmethyl-hexahydro-8B-hydroxy-7-methylene-2R, 2α-phenyl-5H-4aα, 8aβ-1,3-dioxino[5,4-b]pyridine-5-carboxylate (XXA)

To a solution of XIX (40mg, 0.084 mmol) in acetonitrile (2 ml), tetrabutylammonium fluoride (0.5 ml, 1M solution in THF, 0.5 mmol) was added and the contents were refluxed for 18 hr. After cooling to room temperature, the reaction mixture was diluted with ethyl acetate and the organic layer was washed with water and brine. After drying (MgSO$_4$), the solvent was removed and the crude product (32 mg) was chromatographed (silica gel, hexane/ethyl acetate 7/3) to give XXA (21 mg, 65%). $^1$H NMR (CDCl$_3$) 7.51 (m, 2H), 7.37 (complex band, 8H), 5.58 (s, 1H), 5.35 (broad s, 1H), 5.13 (broad s, 1H), 5.12 (s, 2H), 4.81 (dd, J=12, 5 Hz, 1H), 4.61 (d, J=15 Hz, 1H), 4.44 (dd, J=12, 10 Hz, 1H), 4.27 (broad d, J =9 Hz, 1H), 3.63 (dd, J=10, 9 Hz, 1H), 3.55 (d, J=15 Hz, 1H), 3.42 (td, J=10, 5 Hz, 1H), 2.68 (broad s,1H).

EXAMPLE 32

Synthesis of phenylmethyl-hexahydro-8β-hydroxy-7-methylene-2R, 2α-phenyl-5H-4aα, 8aβ-1,3-dioxino[5,4-b]pyridine-5-carboxylate (XXA)

To a solution of IXB (600mg, 1.03mmol) in acetonitrile (5 ml), tetrabutylammonium fluoride (7 ml, 1M solution in THF, 7 mmol) was added and the contents were refluxed for 18 hr. After cooling to room temperature, the reaction mixture was diluted with acetate and the organic layer was washed with water and brine. After drying (MgSO$_4$), the solvent was removed and the crude product (480 mg) was chromatographed (silica gel, hexane/ethyl acetate 7/3) to give XXA (112 mg, 29%) identical to the product of Example 31.

EXAMPLE 33

Synthesis of phenylmethyl 8β-[{(1,1-dimethylethyl) dimethylsilyl}oxy]hexahydro-7-methylene-2R, 2α-phenyl-5H-4aα, 8aβ-1,3 dioxino[5,4-b]pyridine-5-carboxylate (XXB) ,#

To a homogenous solution of XXA (100mg, 0.26 mmol) in methylene chloride (5 ml), N,N-diisopropylethylamine (99%, 140 μl, 0.78 mmol) and tert-butyldimethylsilyl trifluoromethanesulfonate (120 μl, 0.52 mmol) were added. After stirring at room temperature for 2 hr, the reaction mixture was diluted with methylene chloride (700 ml) and washed with aqueous sodium bicarbonate, water and brine. After drying (MgSO$_4$) and filteration, the organic solvent was removed to give XXB (123 mg, purification. 1H NMR (CDCl$_3$) 7.48 (m, 2H), 7.34 (m, 8H), 5.52 (s, 1H), 5.31 (t, J=1.5 Hz, 1H), 5.10 (d, J=12 Hz, 1H), 5.07 (d, J=12 Hz, 1H), 5.06 (broad s, 1H), 4.72 (dd, J=12, 5 Hz, 1H), 4.62 (d, J=14 Hz, 1H), 4.50 (dd, J=12, 10 Hz, 1H), 4.22 (dt, J=8, 1 5 Hz, 1H), 3.58 (dd, J=10, 8 Hz, 1H), 3.43 (broad d, J=14 Hz, 1H), 3.37 (td, J=10, 5 Hz, 1H), 0.86 (s, 9H), 0.03 (s, 3H), −0.03 (s, 3H).

EXAMPLE 34

Synthesis of phenylmethyl 8β-[{(1,1-dimethylethyl) dimethylsilyl)}oxy]tetrahydro-2R,2α-phenylspiro-[5H-4aα, 8aβ-1,3-dioxino[5,4-b]pyridine-7-(6H), 2'-oxiran]5-carboxylate (XXI & XXII)

To a methylene chloride (5 ml) solution of XXB (120 mg, 0.24 mmol), 3-chloroperbenzoic ac (68 mg, 0.31 mmol) was added. The mixture was stirred 20° C. for 20 hr and more 3-chloroperbenzoic acid (75 mg, 0.34 mmol) was added. After 18 hr, the reaction was diluted with methylene chloride and wash aqueous sodium bicarbonate, water and brine. After drying (MgSO$_4$), the solvent was removed and the crude product (120 mg) was chromatographed (silica gel, hexane/ethyl acetate 75/25) to give mixture of epoxides XXI (22mg, 18%) and XXII (70 mg, 57%).

XXI $^1$H NMR (CDCl$_3$) 7.49 (m, 2H), 7.36 (m, 8H), 5.55 (s, 1H), 5.14 (d, J=12 Hz, 1H), 5.07 (d, J=12 Hz, 1H), 4.79 (dd, J=12, 5 Hz, 1H), 4.49 (dd, J=12, 10 Hz, 1H), 3.97 (d, J=8 Hz, 1H), 3.85 (d, J=14 Hz, 1H), 3.71 (dd, J=10, 8 Hz, 1H), 3.39 (td, J=10, 5 Hz, 1H), 3.28 (dd, J=14, 1 Hz, 1H), 3.07 (dd, J=6, 1 Hz, 1H), 2.60 (d, J=6 Hz, 1H), 1.60 broad s, 1H), 0.82 (s, 9H), 0.03 (s, 3H), −0.04 (s, 3H).

XXII $^1$H NMR (CDCl$_{13}$) 7.49 (m, 2H), 7.36 (m, 8H), 5.56 (s, 1H), 5.11 (s, 2H), 4.87 (dd, J=12 , 5 Hz, 1H), 4.55 (dd, J=12, 10 Hz, 1H), 4.07 (d, J=9 Hz, 1H), 3.93 (d, J=15 Hz, 1H), 3.91 (dd, J=10, 9 Hz, 1H), 3.40 (td, J=10, 5 Hz, 1H), 3.37 (d, J=15 Hz, 1H), 3.11 (d, J=5 Hz, 1H), 2.70 (d, J=5 Hz, 1H), 0.82 (s, 9H), 0.01 (s, 3H), −0.07 (s, 3H).

EXAMPLE 35

Synthesis of 1,5-dideoxy-3-O-[(1,1-dimethylethyl) dimethylsilyl]-2-C-methyl-1,5-imino-4,6-O-( R-phenylmethylene)-D-glucitol (XXIII)

To a solution of XXI (22 mg, 0.04 mmol) in tetrahydrofuran (3 ml), lithium aluminum hydride (20 mg, 0.5 mmol) was added. After refluxing for 2 hr, the reaction mixture was cooled to room temperature and diluted with ethyl acetate. After stirring for 15 min., the reaction was carefully quenched by adding drops of 1N HCl and diluted with water. Th was extracted with ethyl acetate and the organic layer was washed with water and brine. After drying (MgSO$_4$), the solvent was removed and the crude product (23 mg) was chromatographed (silica gel, hexane/ethyl acetate 1/1) to give XXIII (8 mg, 57%).$^1$H NMR (CDCl$_3$) 7.48 (m, 2H), 7.37 (m, 3H), 5.46 (s,1H), 4.36 (dd, J=11, 5 Hz, 1H), 3.68 (dd, J=11, 10 Hz, 1H), 3.60 (d, J=10 Hz, 1H), 3.39 (dd, J=10, 9 Hz, 1H), 2.68 (d, J=11 Hz, 1H), 2.22 (d, J=11 Hz, 1H), 2.21(s, 1H), 2.16 (ddd, J=10, 9, 5 Hz, 1H), 1.57 (s, 3H), 0.86 (s, 9H), 0.06 (s, 3H), −0.08 (s, 3H).

EXAMPLE 36

Synthesis of 1,5-dideoxy-2-C-methyl-1,5-[{(phenylmethoxy) carbonyl}imino]-4,6-O-(R-phenylmethylene)-D-mannitol (XXIV)

To a solution of XXII (70 mg, 0.14 mmol) in tetrahydrofuran (5 ml), lithium aluminum hydride (23 mg, 0.57 mmol) was added. After refluxing for 4 hr, the reaction mixture was cooled to room temperature and diluted with ethyl acetate. After stirring for 15 min., the reaction was carefully by adding drops of 1N HCl and diluted with water. Th mixture was extracted with ethyl acetate and the organic layer was washed with water and brine. After drying (MgSO$_4$), the solvent was removed and the crude product (50 mg) was chromatographed (silica gel, hexane/ethyl acetate 1/1) to give XXIV (12 mg, 21%) $^1$H NMR (CDCl$_3$) 7.48 (m, 2H), 7.37 (m, 8H), 5.58 (s,1H), 5.16 (d, J=12 Hz, 1H), 5.10 (d, J=12 Hz, 1H), 4.77 (dd, J=12, 5 Hz, 1H), 4.60 (dd, J=12, 10 Hz, 1H), 4.28 ( d J=14 HZ, 1H), 3.93 (dd, J=10, 9 Hz, 1H), 3.50 (d, J=9 Hz, 1H), 3.23 (td, J=10, 5 Hz, 1H), 2.80 (d, J=14 Hz, 1H), 2.6(broad s, 1H), , 2.32(broad s, 1H) 1.30 (s, 3H).

EXAMPLE 37

Various illustrative compounds synthesized above were tested for inhibition of visna virus in vitro in a plaque reduction assay (Method A) or for inhibition of HIV-1 in a test which measured of cytopathogenic effect in virus-i synctium-sensitive Leu-3a-positive CEM cells grown in tissue culture (Method B) as follows:

METHOD A

Cell and virus propagation

Sheep choroid plexus (SCP) cells were obtained from American Type Culture Collection (ATCC) catalogue number CRL 1700 and were routinely passaged in vitro in Dulbecco's Modified Eagles (DME) supplemented with 20% fetal bovine serum (FBS). SCP cells were passaged once per week at a 1:2 or 1:3 split ratio. Visna was titrated by plaque assay in six-well plates. Virus pools were stored at −70° C.

PLAQUE REDUCTION ASSAY

SCP cells were cultured in 6-well plates to confluence. Wells were washed two times with serum free Minimal Essential Medium (MEM) to remove FBS. 0.2 ml of virus was added per well in MEM supplemented with 4 mM glutamine and gentamycin. After 1 hour adsorption, the virus was aspirated from each well. The appropriate concentration of each compound in 5 ml of Medium 199 (M-199) supplemented with 2% lamb serum, 4 mM glutamine, 0.5% agarose and gentamycin was added to each well. Cultures were incubated at 37° C. in a humidified 5% $CO_2$ incubator for 3-4.weeks. To terminate the test; cultures were fixed in 10% formalin, the agar removed, the monolayers stained with 1% crystal violet and plaques counted. Each compound concentration was run in triplicate. Control wells (without virus) were observed for toxicity of compounds at the termination of each test and graded morphologically from 0 to 4. 0 is no toxicity observed while 4 is lysing of the cell monolayer.

96 well plate assay

The 96 well plate assay was preformed similarly to the plaque assay above with modifications. SCP cells were seeded at $1 \times 10^4$ cells per well in 0.1 ml DME medium. When confluent, the wells were washed with serum free MEM and 25 μl of virus added in M-199 supplemented with 2% lamb serum. After 1 hour, 75 μL of medium containing test compound was added to each well containing virus. After 2-3 weeks incubation the cytopathic effect of the virus was determined by staining with a vital stain. Cell viability was measured by determining stain density using a 96 well plate reader.

Control wells without virus were completed to determine the toxicity of compounds.

METHOD B

Tissue culture plates were incubated at 37° C. in a humidified, 5% $CO_2$ atmosphere and observed microscopically for toxicity and/or cytopathogenic effect (CPE). At 1 hour prior to infection, each test article was prepared from the frozen stock, and a 20 μl volume of each dilution (prepared as a 10×concentration) was added to the appropriate wells of both infected and uninfected cells.

On the 9th day post-infection, the cells in each well were resuspended and a 100 μl sample of each cell suspension was removed for use in an MTT assay. A 20 μl volume of a 5 mg/ml solution of 3-(4,5-dimethylthiazol-2-yl)-2, 5-diphenyltetrazoli (MTT) was added to each 100 μl cell suspension, and the cells were incubated at 37° C. in 5% $CO_2$ for 4 hours. During this incubation MTT is metabolically reduced by living cells, resulting in the production of a colored formazan product. A 100 μl volume of a solution of 10% sodium dodecyl sulfate in 0.01N hydrochloric acid was added to each sample, and the samples were incubated overnight. The absorbance at 590 nm was determined for each sample using a Molecular Devices $V_{max}$ microplate reader. This assay detects drug-induced suppression of viral CPE, as well as drug cytotoxicity, by measuring the generation of MTT-formazan by surviving cells.

Assays were done in 96-well tissue culture plates. CEM cells were treated with polybrene at a concentration of 2 μg/ml, and an 80μl volume of cells ($1 \times 10^4$ cells) was dispensed into each well. A 100 μl volume of each test article dilution (prepared as a 2×concentration) was added to 5 wells of cells, and the cells were incubated at 37° C. for 1 hour. A frozen culture of HIV-1, strain HTVL-III$_B$, was diluted in culture medium to a concentration of $5 \times 10^4$ TCID$_{50}$ per ml, and a 20 μl volume (containing $10^3$ TCID$_{50}$ of virus) was added to 3 of the wells for each test article concentration. This resulted in a multiplicity of infection of 0.1 for the HIV-1 infected samples. A 20 μl volume of normal culture medium was added to the remaining wells to allow evaluation of cytotoxicity. Each plate contained 6 wells of untreated, uninfected, cell control samples and 6 wells of untreated, infected, virus control samples.

Table I, below, sets forth the results of the assay for the compound XVIA, XVIB and XVIC compared to the N-butyl DNJ antiviral agent described in U.S. Pat. No. 4,849,430, which was used as a standard, in Method B: These results are stat terms of the ID$_{50}$ (medium inhibitory dose) and TD$_{50}$ toxic dose).

Anti HIV Activity of 2-Methyl Carbinol Analogs

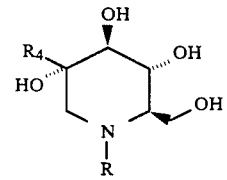

| Compd. (R) | R$_4$ | ID$_{50}$ (μg/ml) | TD$_{50}$ (μg/ml) |
|---|---|---|---|
| n-Bu | H | 34 | >500 |
| XVIA (n-Bu) | Me | 237 | 20% (500) |
| XVIB [(CH$_2$)$_3$Ph] | Me | 492 | 40% (500) |
| XVIC [CH$_2$CH(Et)$_2$] | Me | 6 | 349 |

EXAMPLE 38

Intermediate 2-C-methyl-4,6-O-benzylidene-1-deoxynojirimycin (XIV), prepared in Example 22, above, was tested for inhibition of HIV by the assay of Example 37 and found to have and ID$_{50}$ of 513 μg/ml in Method B.

The antiviral agents described herein can be used for administration to a mammalian host infected with a virus, e.g. visna virus or in vitro to the human immunodeficiency virus, by conventional means, preferably in formulations with pharmaceutically acceptable diluents and carriers. These agents can be used in the free amine form or in their salt form. Pharmaceutically acceptable salt derivatives are illustrated, for example, by the HCl salt. The amount of the active agent to be administered must be an effective amount, that is, an amount which is medically beneficial but does not present toxic effects which overweigh the advantages which accompany its use. It would be expected that the adult human dosage would normally range upward from about one milligram of the active compound. The preferable route of administration is orally in the form of capsules, tablets, syrups, elixirs and the like, although parenteral administration also can be used. Suitable formulations of the active compound in pharmaceutically acceptable diluents and carriers in therapeutic dosage form can be prepared by reference to general texts in the field such as, for example, *Remington's Pharmaceutical Sciences,* Ed. Arthur Osol, 16th ed., 1980, Mack Co., Easton, Pa.

Various other examples will be apparent to the person skilled in the art after reading the present disclosure without departing from the spirit and scope of the invention. It is intended that all such other examples be included within the scope of the appended claims.

What is claimed is:

1. A compound selected from the group consisting of a 2-substituted tertiary carbonyl derivatives of 1-deoxynojirimycin having the formula wherein
R$_4$ = an alkyl, vinyl, alkenyl, alkynyl, aryl, aralkyl, alkenylalkyl, alkynylalkyl or CH$_2$Y substituent having from about 1 to 10 carbon atoms;
Y = OR', SR', NR'R', or N$_3$;
R' = H or CH$_3$; and
R = H or an alkyl, aralkyl, alkenylalkyl, alkynylalkyl, aralkenyl, aralkynyl or hydroxyalkyl substituent, having from about 1 to 18 carbon atoms, provided that no carbon unsaturated bond is directly attached to nitrogen.

2. A compound of claim 1 in which R$_4$ is methyl.
3. A compound of claim 2 in which R is hydrogen.
4. A compound of claim 2 in which R is n-butyl.
5. A compound of claim 2 in which R is 3-phenylpropyl.
6. A compound of claim 2 in which R is 2-ethylbutyl.
7. A compound of the formula wherein W = H, C$_1$-C$_4$ alkyl.

8. A compound of the formula wherein R$_5$ = H, C$_1$-C$_4$ carboxylic acrylic alkanayl.

9. A compound of claim 7 having the formula

10. A compound of claim 8 having the formula

* * * * *